(12) United States Patent
Foster et al.

(10) Patent No.: US 7,585,658 B2
(45) Date of Patent: Sep. 8, 2009

(54) STAPHYLOCOCCUS AUREUS ANTIGENIC POLYPEPTIDES AND COMPOSITIONS

(75) Inventors: Simon Foster, Hathersage (GB); Philip McDowell, Mapperley (GB); Kirsty Brummell, West Bridgford (GB); Simon Clarke, Sheffield (GB)

(73) Assignee: Biosynexus Incorporated, Gaithersburg, MD (US)

( * ) Notice: Subject to any disclaimer, the term of this patent is extended or adjusted under 35 U.S.C. 154(b) by 192 days.

(21) Appl. No.: 11/256,173

(22) Filed: Oct. 24, 2005

(65) Prior Publication Data

US 2006/0140979 A1   Jun. 29, 2006

Related U.S. Application Data

(62) Division of application No. 10/311,879, filed as application No. PCT/GB01/02685 on Jun. 20, 2001, now abandoned.

(30) Foreign Application Priority Data

Jun. 20, 2000   (GB) ................................. 0014907.0

(51) Int. Cl.
*C12N 1/20* (2006.01)
*A61K 39/085* (2006.01)
*C12P 21/04* (2006.01)
*C07K 14/00* (2006.01)

(52) U.S. Cl. ............... 435/252.3; 435/69.7; 435/320.1; 424/243.1; 424/190.1; 530/350

(58) Field of Classification Search ................... None
See application file for complete search history.

(56) References Cited

FOREIGN PATENT DOCUMENTS

EP   0786519 A2   7/1997
WO   WO 99/50418   10/1999

OTHER PUBLICATIONS

Lederman et al (Molecular Immunology 28:1171-1181, 1991).*
Li et al (Proc. Natl. Acad. Sci. USA 77:3211-3214, 1980).*
Cancer Immunity, vol. 2, p. 5 (Jun. 28, 2002).*
Spencer, et al 1990 Dev. Biol. 139, 279-291.*
XP-002278160; Kuroda, M., et al., "Whole Genome Sequencing of Meticillin-Resistant *Staphylococcus aureus*," Lancet, 357:1225-1240 (2001).
XP-002278159; Foster, Simon, "Molecular Characterization and Functional Analysis of the Major Autolysin of *Staphylococcus aureus* 8325/4," *J. of Bacteriology*, 177(19):5723-5725 (1995).
XP-002278161; Kuroda, M., et al., "Nucleotide Substitutions in *Staphylococcus aureus* Strains," *DNA Res.*, 11:51-56 (2004).
XP-002278162: Kuroda, M., et al., "Whole Genome Sequencing of Meticillin-Resistant *Staphylococcus aureus*," Lancet, 357:1225-1240 (2001).
Rahman et al., "Gamma Hemolysin genes in the same familuy with LukF and lukS genes in methicillin resistant *Staphylococcus aureus*," *Bioscience Biotechnology Biochemistry*, 57(7):1234-1236 (1993).
International Search Report, Sep. 18, 2001.
Foster, Simon, "Molecular Characterization and Functional Analysis of the Major Autolysin of *Staphylococcus aureus* 8325/4," *J. of Bacteriology*, 177(19):5723-5725 (1995).
*Cancer Immunity*, 2:5 (Jun. 28, 2002).
*Infect. Immun.*, 62(5):1843-7 (1994).
Rudinger et al., "Peptide Hormones," Parsons, J.A., University Park Press, 1976, 1976 pg.
Burgess et al., *J. Cell Biology*, 111:2129-2138 (1990).
Lazar et al., *Molecular and Cellular Biology* 8(3):1247-1252 (1988).
Jobling et al., *Mol. Microbiol.*, 5(7):1755-67 (1991).
Oshida et al., *Proc. Natl. Acad. Sci.*, 92(1):285-289 (1995).
Database EMBL [Online] Jul. 3, 2000, "Staphylococcus aureus sai-1 gene for 29-kDa cell surface protein, complete cds." XP002445369 retrieved from EBI accession No. EMBL:AB042826 Database accession No. AB042826.

* cited by examiner

*Primary Examiner*—Robert B Mondesi
*Assistant Examiner*—Padma V Baskar
(74) *Attorney, Agent, or Firm*—Casimir Jones S.C.

(57) ABSTRACT

The invention relates to a method for the identification of antigenic polypeptides expressed by pathogenic microbes; vaccines comprising such polypeptides; recombinant methods to manufacture such polypeptides; and therapeutic antibodies directed to such polypeptides.

6 Claims, No Drawings

SEQUENCE LISTING

<160> NUMBER OF SEQ ID NOS: 32

<210> SEQ ID NO 1
<211> LENGTH: 2260
<212> TYPE: DNA
<213> ORGANISM: Staphylococcus aureus

<400> SEQUENCE: 1

```
gatcttaatg aaagagtgac tgatgcctta gcaattgcta gttgtatcaa tgcgcatccg      60
tatgtcaaag gagaactttg cgtgtccgat gacttaacgt atacgacagg ttattttgcc     120
gctgctaaaa ttggttacca tcgattattt gatattaaac cagttaatac gagatatgga     180
ggcagaataa tatttgtgga cgattgtatt gatttaaatc attacatatc attttagaa     240 agcacaccga agcaagttgt ttatgaaacg gtataggggt tttagtatga catcaaaaga     300
tattactcaa attagtgtca ttgctgcgat tttaaccatt ttggcagttt tgaaaatacc     360
gtccattata ccaggattag attttcaatt atctgcaccg gcagcattat tgatattagc     420
tttctttgga attaaaaagt acttttttagg tggattatta tctagcctat tattactagt     480
atttggcgta tttaatccaa ttaatgtgat tatctctatt atatttagag ttatagctat     540
tgcagttgtt tatttattga aaataaatgt actatcatta gttttagcaa gtgtattagg     600
cagtttggta tataggctac tattatctat tatttttaaat ttacctgtgt gggtagtgtt     660
gttaaacgcg attccaggcg taatattcac tttaattgta gctattcctt tatatctcac     720
attgagaaaa agaatggcag tattactaag ataataaatc aaaacacggt cgtcacaatt     780
actgttggcg accgtgtttt actagctatt tattgttttc agtttctttt gtatctaaca     840
atttcacttt gtgattttcc caatcaattt catatgttga tttaaatgtt ctagttttaa     900 agttttata atttgcgcct gcccagtaga agccattcca acgaatttgg tataaatcca     960
tttcacgttg ataagttact gtaattttag attttttagc gccatcttgt ctgtgtgata    1020
gtacgcttaa aaattctgga ttgaagttac ttctagataa taatggcatt tggtgttgcg    1080
ctatgaagtt ttggccagcg tatgcactgc tttgtctgcc agctaagaag agttcattac    1140
catatgttgg gtggaagcta tctcttccat aaggtcccca accattattc ataatttat     1200 gtgcttcaac tccccagcca acattttat aatttgtgtt gcgacttaat gttgttctgt    1260 aacttttcttg tttataatta attgtttcag aaaaagctgt atttccatta agtccaccag    1320
ataaaccatt agagatacta atgtcaccac caaatgtata gcctaaagta ttttgaactt    1380
gaaactcttc attttgattt tttggtgcat aatcaacgac gtttactgaa tcattagatt    1440
```

-continued

```
gtgagcttat agatacattg tatttagctc cccaatataa ttttgaaaag tcatagtcat    1500
taggattagg tttcacaaag cctgagttaa tattcccagt agctttaagt actaaagtat    1560
ctttatcata acttttatct ttgatgaaat taaatgttaa aatctgtgaa attttaaatt    1620
tatcagaatc tgctgtggct gttgttttgt ataaagtaac tttgtcatcg acttttttta    1680
cgctgactgg tgttatttta ccttcagcat tagcagtacc agaaagtaat aataatgcca    1740
tagatgtagc aacggatgat ttgactaatt tattcatttt catatcaatt ctgtcctttc    1800
accttgattt catgagtctt ccaattgacc tcgtatttca cagtatagtt tctatttaca    1860
aatgcattat ggactctatg tccgtctaaa taactgttgc cataatgcgt tgatctttta    1920
atggcatgag tgcatccat gtttcttccg taagtaattt caaattcgct tgtatcgctt    1980
gaaccttttt catgagatac tgtggcgata atgaagggt taaatccact ttgtacaaga    2040
ggtggtaact cactgtctgg aacgaaataa tctctaggat ctttactatg aggtttgtag    2100
cctacaaata aatcgctatc aaaggctgat ttttgacctg attcagtggc gaatgaattc    2160
gctttgacgc cccataaaac actttttgag ttttgttgtt ctacttcact tacataattt    2220
tgttgtgtat agctaatcga tttagaatag ttaaatgatc                         2260
```

<210> SEQ ID NO 2
<211> LENGTH: 2902
<212> TYPE: DNA
<213> ORGANISM: Staphylococcus aureus

<400> SEQUENCE: 2

```
gatcgtataa tcgaaacagc accaacggat tacttatctt ggggtgtcgg tgcagtcggt     60
aaccctagat tcatcaatgt tgaaatcgta cacacacacg actatgcttc atttgcacgt    120
tcaatgaata actatgctga ctatgcagct acacaattac aatattatgg tttaaaacca    180
gacagtgctg agtatgatgg aaatggtaca gtatggactc actacgctgt aagtaaaatat    240 ttaggtggta ctgaccatgc cgatccacat ggatatttaa gaagtcataa ttatagttat    300
gatcaattat atgacttaat taatgaaaaa tatttaataa aatgggtaa agtggcgcca    360 tggggtacgc aatctacaac tacccctact acaccatcaa aaccaacaac accgtcgaaa    420
ccatcaactg gtaaattaac agttgctgca acaatggtg tcgcacaaat caaaccaaca    480
aatagtggtt tatatactac tgtatacgac aaaactggta agcaactaa tgaagttcaa    540 aaaacatttg ctgtatctaa aacagctaca ttaggtaatc aaaaattcta tcttgttcaa    600
gattacaatt ctgtaataa atttggttgg gttaaagaag gcgatgtggt ttacaacaca    660
gctaaatcac ctgtaaatgt aaatcaatca tattcaatca aacctggtac gaaactttat    720
acagtacctt ggggtacatc taaacaagtt gctggtagtg tgtctggctc tggaaaccaa    780
acatttaagg cttcaaagca acaacaaatt gataaatcaa tttatttata tggctctgtg    840
aatggtaaat ctggttgggt aagtaaagca tatttagttg atactgctaa acctacgcct    900
acaccaacac ctaagccatc aacacctaca acaaataata aattaacagt ttcatcatta    960
aacggtgttg ctcaaattaa tgctaaaaac aatggcttat tcactacagt ttatgacaaa    1020
actggtaagc caacgaaaga agttcaaaaa acatttgctg taacaaaaga agcaagttta    1080
ggtggaaaca aattctactt agttaaagat tacaatagtc aactttaat tggttgggtt    1140 aaacaaggtg acgttattta taacaatgca aaatcacctg taaatgtaat gcaaacatat    1200 acagtaaaaac caggcactaa attatattca gtaccttggg gcacttataa acaagaagct    1260
ggtgcagttt ctggtacagg taaccaaact tttaaagcga ctaagcaaca acaaattgat    1320
```

-continued

```
aaatctatct atttatttgg aactgtaaat ggtaaatctg gttgggtaag taaagcatat    1380
ttagctgtac ctgctgcacc taaaaaagca gtagcacaac caaaaacagc tgtaaaagct    1440
tatactgtta ctaaaccaca aacgactcaa acagttagca agattgctca agttaaacca    1500
aacaacactg gtattcgtgc ttctgtttat gaaaaaacag cgaaaaacgg tgcgaaatat    1560
gcagaccgta cgttctatgt aacaaaagag cgtgctcatg gtaatgaaac gtatgtatta    1620
ttaaacaata caagccataa catcccatta ggttggttca atgtaaaaga cttaaatgtt    1680
caaaacttag gcaaagaagt taaaacgact caaaaatata ctgttaataa atcaaataac    1740
ggcttatcaa tggttccttg gggtactaaa aaccaagtca ttttaacagg caataacatt    1800
gctcaaggta catttaatgc aacgaaacaa gtatctgtag gcaaagatgt ttatttatac    1860
ggtactatta ataaccgcac tggttgggta atgcaaaag atttaactgc accaactgct    1920
gtgaaaccaa ctacatcagc tgccaaagat tataactaca cttatgtaat aaaaatggt    1980 aatggttatt actatgtaac accaaattct gatacagcta atactcatt aaaagcattt    2040 aatgaacaac cattcgcagt tgttaaagaa caagtcatta atggacaaac ttggtactat    2100
ggtaaattat ctaacggtaa attagcatgg attaaatcaa ctgatttagc taaagaatta    2160
attaagtata atcaaacagg tatggcatta aaccaagttg ctcaaataca agctggttta    2220
caatataaac cacaagtaca acgtgtacca ggtaagtgga caggtgctaa cttaatgat    2280 gttaagcatg caatggatac gaagcgttta gctcaagatc cagcattaaa atatcaattc    2340
ttacgcttag accaaccaca aaatatttct attgataaaa ttaatcaatt cttaaaaggt    2400
aaaggtgtat tagaaaaacca aggtgctgca tttaacaaag ctgctcaaat gtatggcatt    2460
aatgaagttt atcttatctc acatgcccta ttagaaacag gtaacggtac ttctcaatta    2520
gcgaaaggtg cagatgtagt gaacaacaaa gttgtaacta actcaaacac gaaataccat    2580
aacgtatttg gtattgctgc atatgataac gatccttta cgtgaaggtat taaatatgct    2640 aaacaagctg gttgggacac agtatcaaaa gcaatcgttg gtggtgctaa attcatcggc    2700
aactcatatg taaagctgg tcaaaataca ctttacaaaa tgagatggaa tcctgcacat    2760
ccaggaacac accaatatgc tacagatgta gattgggcta acatcaatgc taaaatcatc    2820
aaaggctact atgataaaat tggcgaagtc ggcaaatact tcgacatccc acaatataaa    2880
taagcaacat gaacatagga tc                                             2902
```

<210> SEQ ID NO 3
<211> LENGTH: 2792
<212> TYPE: DNA
<213> ORGANISM: Staphylococcus aureus

<400> SEQUENCE: 3

```
gatcaactta atataatgaa ttcggcaaca gaagagcatc atcataaaga ttatattaaa      60
ctatataatt taggtggcgg tgctgctaaa aaaattgcaa tagaggtttt attggggaag     120
gataaagtca ttcagaaaaa atacgtgcat attttaccta gtaaagaagg gtacatgtta     180
ccaattaata aaaatgtgta cgaagaatta gaaagaacga ttgagaacaa tggtcatgaa     240
gctgatttga atgtacgtat gacttattat cataatgtaa gtcgcaaaca acaggaagtt     300
atattaaaag gtcaaatcga ccgttttaat acttataata ataagaaat ttatgatttg     360 cagtttatct aaaaattgat ttaagagggt agttgtttat tgcgaaaaat atcattcaat     420
tttaatgaaa aatggcgtc attactataa aatattactt tatgttgtaa tgcatttttc     480
tataagatag aactaaaagg agggggcaaag atgcaaatta gacaaataca tcaacatgac    540
```

-continued

```
tttgctcaag tggaccagtt aattagaacg gcatttgaaa atagtgaaca tggttatggt    600
aatgaatcag agctagtaga ccaaattcgt ctaagtgata cgtatgacaa taccttagaa    660
ttagtagctg ttcttcaaaa tgaagttgta gggcacggtt tactaagtga agtttatctt    720
gataacgagg cacaacggga aattggatta gtgttagcac ctgtatctgt tgatattcat    780
catcaaaata aaggtattgg gaagcgattg attcaagcat tagaacgaga agcaatatta    840
aaaggatata attttatcag tgtattagga tggccgacgt attatgccaa tctaggatat    900
caacgcgcaa gtatgtacga catttatcca ccatatgatg gtataccaga cgaagcgttt    960
ttaattaaag aattaaaagt gaacagttta gcgggaaaaa caggtaccat aaattacaca   1020
tctgcttttg aaaaaatatg atttcaagct aggattacat taggtagagt tcatattaat   1080
aataaaaaat gtttgcaatc aaatcgtacg ttgtcgtttg taattcttaa aatagcaata   1140
aataaaatgt ttgttagtaa agtattattg tggataataa aatatcgata caaattaatt   1200
gctataatgc aattttagtg tataattcca ttaacagaga ttaaatatat ctttaaaggg   1260
tatatagtta atataaaatg acttttttaaa aagagggaat aaaatgaata tgaagaaaaa   1320
agaaaaacac gcaattcgga aaaaatcgat tggcgtggct tcagtgcttg taggtacgtt   1380
aatcggtttt ggactactca gcagtaaaga agcagatgca agtgaaaata gtgttacgca   1440
atctgatagc gcaagtaacg aaagcaaaag taatgattca agtagcgtta gtgctgcacc   1500
taaaacagac gacacaaacg tgagtgatac taaaacatcg tcaaacacta ataatggcga   1560 acgagtgtg gcgcaaaatc cagcacaaca ggaaacgaca caatcatcat caacaaatgc   1620
aactacggaa gaaacgccgg taactggtga agctactact acgacaacga atcaagctaa   1680
tacaccggca acaactcaat caagcaatac aaatgcggag gaattagtga atcaaacaag   1740
taatgaaacg acttctaatg atactaatac agtatcatct gtaaattcac ctcaaaattc   1800
tacaaatgcg gaaaatgttt caacaacgca agatacttca actgaagcaa caccttcaaa   1860
caatgaatca gctccacaga gtacagatgc aagtaataaa gatgtagtta atcaagcggt   1920
taatacaagt gcgcctagaa tgagagcatt tagtttagcg gcagtagctg cagatgcacc   1980
ggcagctggc acagatatta cgaatcagtt gacgaatgtg acagttggta ttgactctgg   2040
tacgactgtg tatccgcacc aagcaggtta tgtcaaactg aattatggtt tttcagtgcc   2100
taattctgct gttaaaggtg acacattcaa aataactgta cctaaagaat aaacttaaa    2160 tggtgtaact tcaactgcta aagtgccacc aattatggct ggagatcaag tattggcaaa   2220
tggtgtaatc gatagtgatg gtaatgttat ttatacattt acagactatg taaatactaa   2280
agatgatgta aaagcaactt tgaccatgcc cgcttatatt gaccctgaaa atgttaaaaa   2340
gacaggtaat gtgacattgg ctactggcat aggtagtaca acagcaaaca aaacagtatt   2400
agtagattat gaaaaatatg gtaagtttta aacttatct attaaaggta caattgacca    2460
aatcgataaa acaaataata cgtatcgtca gacaatttat gtcaatccaa gtggagataa   2520
cgttattgcg ccggttttaa caggtaattt aaaaccaaat acggatagta atgcattaat   2580
agatcagcaa aatacaagta ttaaagtata taaagtagat aatgcagctg atttatctga   2640
aagttacttt gtgaatccag aaaactttga ggatgtcact aatagtgtga atattacatt   2700 cccaaattcca aatcaatata agtagagtt taatacgcct gatgatcaaa ttacaacacc   2760
gtatatagta gttgttaatg gtcatattga tc                                 2792
```

<210> SEQ ID NO 4
<211> LENGTH: 2478
<212> TYPE: DNA
<213> ORGANISM: Staphylococcus aureus

<400> SEQUENCE: 4

| | | | | | | |
|---|---|---|---|---|---|---|
| gatcgaattg | aacgaagcat | ttgcttctca | aacgattgca | tctattaaag | aagtaggtct | 60 |
| agatatatca | cgtacgaatg | tgaatggtgg | cgctattgct | ttaggtcatc | cattaggtgc | 120 |
| tacaggcgca | atgttaaccg | cgcgtttact | taatgaaatg | ggtagacgtc | ccgatagccg | 180 |
| ttacggcatg | gttacgatgt | gtattggtgt | cggcatgggt | gcagctgcta | tatttgaata | 240 |
| tgtgcgttag | aatggttgat | tttggatgaa | gcggattcgt | tttgttattg | aatgaagtag | 300 |
| gctgaagttg | aagccagttg | aagttgaagc | gggttgaagc | aatttcgttt | tattaatgaa | 360 |
| gctgtgtgaa | atatagtgat | tgaacaaaaa | agtggtttaa | tgggatggtg | gttatttccg | 420 |
| ttttagaatt | taacatttac | acgtctaatt | ttaatcattg | ttttaaattt | tatgaatcga | 480 |
| agcccttga | tttaataata | tttgctaatg | ctagtaactt | atctgattgt | tcatgtttaa | 540 |
| aataagaaa | accactcaca | tcagtgtgtg | ttcgaactag | acttgtaagt | tccagttcgg | 600 |
| cacgactttc | taaagcaatt | attattgctg | tgattgtcgt | atatcactta | gatgtgcgtg | 660 |
| gtttatttta | ataggttagt | aatatattag | gtcatgttat | gtttaagact | ataatgaata | 720 |
| aataatttag | aaatatgctt | ccgattgttc | gatgctttaa | ttcagttaga | agcatcatag | 780 |
| aatgcatgat | tactgttgta | aagatacgta | atgttttgta | ttgactgtat | gtctttggat | 840 |
| agagttacaa | acttattttg | ttactctagg | cccatatgtc | gcagtaccat | ctgcatgtgt | 900 |
| tgttacattg | tatgcatttg | ttttacttgg | cttcttgtat | gtcgggcgag | ctccgtatga | 960 |
| cacttgaccg | tttgcatgtg | ttgttacgtt | gtatgcattt | gttttgcttg | gcttgttttg | 1020 |
| tgttgggcga | gcgccatatg | atacttggcc | gtttccatgt | gttgttacgt | tatatgcgtt | 1080 |
| tgttttgctt | ggcttgtttt | gtgtcggacg | agctccgtat | gatacttggc | cgtttgcatg | 1140 |
| tgttgttaca | ttgtatgcat | tcgtttcgct | tggcttcttg | tatgtcggac | gagctccgta | 1200 |
| tgatacttga | ccatttgcat | gtgttgttac | gttatatgca | tttgtttctg | atggcttatt | 1260 |
| gaatcttggt | ctcgcttcat | atccaaatgt | tccatcgttg | tattcacgga | tacctgtacc | 1320 |
| agcatctcta | tatttaacat | atttaggtgt | tttgttaaat | tgcggtctcg | gaccatattg | 1380 |
| agaagcttct | gttgtttcag | ttgcttgagg | tttaacttca | atatcacttg | attctccttg | 1440 |
| agtacctttt | aacgttgatt | cagtaccttg | tggttttatt | tcaagtttag | atgagctacc | 1500 |
| ttcaagacct | tctaaaatag | ggttcgttaa | cggtgggttt | gtataattat | tgcttaatga | 1560 |
| tgggccgctt | tgttccattg | ttagaaaatc | gggaccttga | acgatttcac | cttgtaccgt | 1620 |
| tttattttcc | atcgttggat | attccggacc | ttttacaatt | tcacctgtaa | ttgtgccctg | 1680 |
| tggaatttta | actaatggtt | gtgcaactgg | ttgtgttgtt | tcttcagctt | taccagccgt | 1740 |
| agttttaacc | tcttgttggt | tatcaacttt | aggtgcttga | ggttcttcaa | ctttcttctc | 1800 |
| ttcttttact | actggcgatt | ttgtttcagt | ttctccgtat | ttttgacag | ttttcttttt | 1860 |
| ccaagaatca | tctgcttctt | taactgcttt | tttcgttct | tcaactaatt | tatcaaaatt | 1920 |
| aggtttatta | tcactatttg | ttttatagtt | atgtgttgta | ggattatatt | tcgttataga | 1980 |
| tttcggtcta | ttttgtttag | tttccataaa | gaaatcatca | ataattgaat | ttaagtcatc | 2040 |
| aatcatttct | tttttaatac | gttcattgt | aattttatgt | ggattgtctg | tatctccaag | 2100 |
| gattaagtcc | agttttgctc | gtaactcttt | cgcgtgctcc | ccataatcct | tatcaccata | 2160 |

```
atatgataca actaatgtat caatttcaga tacgagatcg tatacttcct tagttgcttt    2220
atcttcttct gctgcattaa aagttttcaa gtctgaattc ttatccttaa tatctttaac    2280
ttctctgtga aaatcatcca gtgctctctt taatgcatcc tgtagttcat tgtattcttt    2340
catcgaaagt tcttctaaat tatatttatg aaaattagcc attttttaaat ctgtacgagg   2400 attttctttt ttataatttg cataccattg tttataatct tcatattgag atttctttct    2460
ctccaaaaga tattgatc                                                  2478

<210> SEQ ID NO 5
<211> LENGTH: 2070
<212> TYPE: DNA
<213> ORGANISM: Staphylococcus aureus

<400> SEQUENCE: 5
tgacgctgct tttgtaaata catataattt ttccacttca tgatttaatt cgttcgcatg      60
atctttgtaa tttctaccaa aagcaatcac attattcgga ggtgttactg gtggtaaaaa     120
ttcaatgtca ttaaatgaaa ttttatagtc ttcagctttg ccgctatctt ctgctgctac     180
aactgcttta cgtacttgtt cttgaaaatc taaagtatga ttttgttgta aaccagctaa     240
caatgtttta ggatggaaat ctccttctgc aaagtcagca atacttgtg ttaaatccca      300 tacagcatct tcgcgtttta ctttaacgcc atatgaagtt ttgtcattat acttgaatga    360
taagaatttc attcattctc aactcctcgt ctttatctta attcacatta aactttttt     420 cgttatcaaa taacaaataa ataagtaaga caattttgaa aatgagttgt gttcattctg     480
ctacaaggac tttgcactta atcgaaatta ttttttattc ttttgaaaat caaaatacta     540
tagttgcaat gtaccaaatt tgaagaagta taaataaccct ttaacttctt tattaagaat    600
cgtttgaagc gtattttgat aatatttcat ctgtatctta tatttatttt ttaattgtgt    660 accaattctct tcatctgtca tcccacggcg acgattaaat gcatcggttt tatagtctac    720
aaaataatgc acaccatctt taacaaagat taagtcaatc ataccttgaa taattgagac    780
gtcttcgtct ccttgtggca attggtcaac taatgcttgg ttaactacaa acggtaattc    840
acgataaact tgctctgctt cagcaataat cgaatataac tcactattga taaatgtcat    900
tatttcatcc atacggatat cttttttttcgc atctgcttcg ataatatgtt tatcgattaa   960
tccatcgata tactgatgta actcaacttc agatatgcgt tcttttttga atggtaaatg    1020
ttgcatcact gtatgcatta acgtaccaat tcattcgct tttcgtttac cttgttcact     1080
tagaaattta ggtcgttcat acgttgaaaa accgatacga tattgcctta ctcgttcgta   1140
acttgtgcca ctttcttctg tttcatattg tcttttcaat tcagaaacag attgttttga   1200
gggcttttta gtatcattta catatggata tcgataatca agttggtgtt taatttgtgc    1260
tttaacatct tcattaccat tttgcatagt ttctaattga ttaaccgaac gatattcatc    1320
attatctaaa atggtttctg tagacacatc ttcaaagtac acaattgaaa tatttacatt    1380
cggacgacta ctatcttcaa tttgtgctat atctttttca aattttaaat catctggaat    1440
tgacgcagat tgatgtttag ataaaatact ataaataaga tggaacggat ttggtgaagt    1500
taatcgttca ttgacagcaa tgtgctcacc agaaatagac aattgctcta gttctagtaa    1560
tgatttatca tttttcactc taccaattaa ataagttgt tctttcgctc ttgttaatgc     1620
tacatagact aatcgcattt cttctgacac aagttctttt tcggcaacag ctctatatgc    1680
aaccgaagct aaagatggaa atgccatttc tttatccaca tcaaaataat ccattccgag    1740
accaaattgc tgatttaaaa taactggttg tttcaaatca cgtttattaa aatctttga    1800
```

-continued

| | |
|---|---|
| caatccagaa taaatgacaa atggaaactc tagaccttta ctactatgaa ttgtcatcat | 1860 |
| tctaacgaca ttatcgtttg gaccaactac attttcctca ccaaaatctt tgcctctttc | 1920 |
| aatcaattca tcgataaaac gaataaattg atataaacct ctaaaacttg aattctcaaa | 1980 |
| ctcgatagct ttattaaata aaccataaag atttgcacgt cgtccacgtc caccaataag | 2040 |
| tccactaaag tattgaataa cataatgatc | 2070 |

<210> SEQ ID NO 6
<211> LENGTH: 2394
<212> TYPE: DNA
<213> ORGANISM: Staphylococcus aureus

<400> SEQUENCE: 6

| | |
|---|---|
| gatcagattt attagacagt attccagata tacccacacc aaagccagaa aagacgttaa | 60 |
| cacttggtaa aggtaatgga ttgttaagtg gattattaaa tgctgatggt aatgtatctt | 120 |
| tgcctaaagc gggggaaacg ataaaagaac attggttgcc gatatctgta attgttggtg | 180 |
| caatgggtgt actaatgatt tggttatcac gacgcaataa gttgaaaaat aaagcataat | 240 |
| tatattgggg gaagagcatc tatatatttt tttaagtata taagacgtct tatttcccct | 300 |
| taatttattg tgaagtatat gcaaaatgca atgaatagat tgtccatcat tttaacgtta | 360 |
| taatgaattt aacgacttag aactacacaa gtaaaggaga atgaagatgt ctcgaaaaac | 420 |
| ggcgctatta gttttggata tgcaagaagg tatagcgagt agtgtaccta gaataaaaaa | 480 |
| tattattaaa gcgaatcaga gagcaattga agcagcaaga caacatcgaa taccagtcat | 540 |
| tttcatacgt ttagtgttag ataagcattt taatgatgtc tcctcgagta ataaagtgtt | 600 |
| ttcaacaatt aaagctcaag gatatgcgat tactgaagca gatgcatcta cacgaatact | 660 |
| tgaagattta gcaccactag aagatgagcc gattatttct aagcgacgct ttagcgcatt | 720 |
| tacaggtagt tacttggaag tttatttacg tgcaaatgat attaatcatt tagtattaac | 780 |
| gggtgtctct acaagtggag ctgtattgag cacggcatta gaaagtgtag ataaagacta | 840 |
| ttatattact gttttagaag atgctgttgg tgatagatca gatgataaac atgactttat | 900 |
| tattgaacaa atttttatcac gctcatgtga cattgaatcc gtagagtcat ggaaaagtag | 960 |
| tttatagtta atataacgtc aattaaagct cggcagtaat gtttgagaat aagtacatt | 1020 |
| gctcatattt ataaaatgtg tgagatggca attgaaacgg atatgatgag gaacatttga | 1080 |
| acataaaata atatatttat ataaaacgac ccgaggcgtt cgaactgaat gcctcgggtt | 1140 |
| taattgaata agaaatcgga cttatgaaca gaaatatgtt taagtccgaa ctccttgttt | 1200 |
| atacttataa atttttacggg tttaataaa tacttattta cctgtaatat atgataattc | 1260 |
| ttcagcggca gctgcgttga tagttctatg agaaatgata cctaatcctt taacattgga | 1320 |
| ttctgaaata acgatagaac catcactgtt aacttttttca acaaatgcta catgaccgta | 1380 |
| atgttgatct gcaccaaatt gtccagcctc aaatacaaca gcagcatgac gttttggtgt | 1440 |
| atgacttact tgataatcac ggtattgagc tcgattattc caattatgtg catcacctaa | 1500 |
| atcacctgag atagatgtac caaattgttt catacggtta tatacgtacc aagtacattg | 1560 |
| gccatgtgga tatggcatac tatcagatac ctcacggaaa ggtttgaatt catctgatga | 1620 |
| atcatcataa tccttgatag aacgttcata tttatctaaa tctggcatgc gttcatcgtc | 1680 |
| aaactgagtt aattgatagt gtttaataat actgtttaat ttcttagcat agtttggatc | 1740 |
| tgtagcatat gttttagata agtgtgatgt tgcatctttt taagaatcgg cttccgattt | 1800 |
| ccatgttggt ttataaattg ttcgattgcc atcaatacca tttttaataa ggtcagagta | 1860 |

-continued

| | |
|---|---|
| atcttttagt gattctttcg tgcttggata ttttcggaat ccagcattaa tactatacaa | 1920 |
| ttgattacca tcagcttcta atgtgttaaa aggaacagaa ttcccttcaa aagcaccttt | 1980 |
| gataccgaat aaattatggt ttggtgactt agctaaagca ctacgacctg agtcagattc | 2040 |
| taagattgct tgggcaatca tgacagacgc ataaatatcg ttatcttgac caatgcgatg | 2100 |
| tgcatcttta gcaattgatt tgacaaattg acgtgtatct tttgagtcaa caacgttaaa | 2160 |
| ttgtccgcta tcatcattgt tagatatact aggatctgtt tcgaataatg atgttgcacg | 2220 |
| tgtatccttt tgattaacat cgttattgaa tgattgagca ggtttagatt tatgtttcaa | 2280 |
| ttcatcttgt gttggtaact gtggattctt tgtattagat ttttcatttt tgtctttttt | 2340 |
| agattgagat gcataatctt tttgtgtttt ctttgcatct tcactgtatt gatc | 2394 |

<210> SEQ ID NO 7
<211> LENGTH: 2033
<212> TYPE: DNA
<213> ORGANISM: Staphylococcus aureus

<400> SEQUENCE: 7

| | |
|---|---|
| gatctggaac aggtttcatt gtcggtaaaa atacaattgt taccaacaag catgtcgttg | 60 |
| caggtatgga aattggtgca catattatag cgcatcccaa tggtgaatat aataatggcg | 120 |
| gattttataa agttaaaaaa attgtccgtt attcaggtca agaagatatt gccattctac | 180 |
| atgtggaaga taaagctgtt catccaaaaa acaggaattt taaagattac acaggcattt | 240 |
| taaaaatagc atcagaagct aaagaaaatg aacgcatttc aattgttggc tatccagaac | 300 |
| catatataaa taaatttcaa atgtatgagt caacaggaaa agtgctgtca gttaaaggca | 360 |
| acatgattat tactgatgct ttcgtagaac caggcaactc aggttcagct gtatttaaca | 420 |
| gtaaatacga agttgtaggt gttcactttg gtggaaacgg ccctggaaat aaaagtacaa | 480 |
| aaggatatgg tgtttatttc tctcctgaaa ttaagaaatt cattgcagat aacacagata | 540 |
| aataaatcct tacatagata aatgattta aaaattaaca acaaactcaa caattcaaat | 600 |
| catctctgtg attccattta ttcgaaatga ttaaaaaaaa taaacttca aaaagctaac | 660 |
| attataatta tacaaatact tagaggagca gaaaaatgaa taaaaatata atcatcaaaa | 720 |
| gtattgcagc attgacgatt ttaacatcaa taactggtgt cggcacaaca atggttgaag | 780 |
| gtattcaaca aacagccaaa gccgaaaata ctgttaaaca aattacaaat acaaatgttg | 840 |
| caccatacag tggtgttaca tggatgggcg ctggaacagg atttgtagtt ggaaatcata | 900 |
| caatcattac caataaacat gttacctatc acatgaaagt cggtgatgaa atcaaagcac | 960 |
| atcctaatgg ttttttataat aacggtggtg gactttataa agttactaag attgtagatt | 1020 |
| atcctggtaa agaagatatt gcggttgtac aagttgaaga aaaatcaaca caaccaaaag | 1080 |
| gtagaaaatt caaagatttc actagtaaat ttaatatagc atcagaagct aaagaaaatg | 1140 |
| aacctatatc agtcattggt tatccaaatc ctaatgaaa taaactacaa atgtatgaat | 1200 |
| caactggtaa agtattatca gtgaatggga atatagtgtc ttcggatgca attattcagc | 1260 |
| ctggtagctc tggttcacct atattaaata gtaaacacga agctattggt gtaatctatg | 1320 |
| ccggtaataa gccatcaggt gaaagcacaa gaggatttgc tgtttatttc tctcctgaaa | 1380 |
| ttaagaaatt cattgcagat aatttagata ataattaaa acttagacat tcacccaatc | 1440 |
| ctgacaaaat atactataac taacattttat taatatatat tgcattattt aatatgcatc | 1500 |
| aaagccaatc aacgattgat tttcaccaac tcaattgttg attggtttta tttatgtatg | 1560 |
| aatgaacaac ttttttgacat cattaagaat ataaatgatt ttgaaagcat ttgaaagcta | 1620 |

-continued

```
caacatttct ataaaattt tcaataacaa ttgcgccact aaaactcaaa atttccacca      1680
ccaacatcca aattatcaac atcgcaacat aaccaaatgt tataataaat ctattacaca      1740
aagagataaa ttacttatgc aaaggcggag gaatcacatg tctattactg aaaaacaacg      1800
tcagcaacaa gctgaattac ataaaaaatt atggtcgatt gcgaatgatt taagagggaa      1860
catggatgcg agtgaattcc gtaattacat tttaggcttg attttctatc gcttcttatc      1920
tgaaaaagcc gaacaagaat atgcagatgc cttgtcaggt gaagacatca cgtatcaaga      1980
agcatgggca gatgaagaat atcgtgaaga cttaaaagca gaattaattg atc            2033
```

<210> SEQ ID NO 8
<211> LENGTH: 2794
<212> TYPE: DNA
<213> ORGANISM: Staphylococcus aureus

<400> SEQUENCE: 8

```
gatcaaacgt tgcttaactt cttttaatg cttaaaaatt atttcaaagg cacatagaaa        60
cgctatatta atctcatact cactcattat tttttgctta aattacttaa taatacttca      120
ataattgtta aaagggtttt aatgtgatta tcttagaacg ccatctataa tgatgttgta      180
tgattcaaat tacgtaaaaa gacaatcgaa tataatatag attggagcat acaattatga      240
aaatgagaac aattgctaaa accagtttag cactagggct tttaacaaca ggcgcaatta      300
cagtaacgac gcaatcggtc aaagcagaaa aaatacaatc aactaaagtt gacaaagtac      360
caacgcttaa agcagagcga ttagcaatga taaacataac agcaggtgca aattcagcga      420
caacacaagc agctaacaca agacaagaac gcacgcctaa actcgaaaag gcaccaaata      480
ctaatgagga aaaaacctca gcttccaaaa tagaaaaaat atcacaacct aaacaagaag      540
agcagaaaac gcttaatata tcagcaacgc cagcgcctaa acaagaacaa tcacaaacga      600
caaccgaatc cacaacgccg aaaactaaag tgacaacacc tccatcaaca aacacgccac      660
aaccaatgca atctactaaa tcagacacac cacaatctcc aaccataaaa caagcacaaa      720
cagatatgac tcctaaatat gaagatttaa gagcgtatta tacaaaaccg agttttgaat      780
ttgaaaagca gtttggattt atgctcaaac catggacgac ggttaggttt atgaatgtta      840
ttccaaatag gttcatctat aaaatagctt tagttggaaa agatgagaaa aaatataaag      900
atggacctta cgataatatc gatgtattta tcgttttaga agacaataaa tatcaattga      960
aaaaatattc tgtcggtggc atcacgaaga ctaatagtaa aaagttaat cacaaagtag      1020 aattaagcat tactaaaaaa gataatcaag gtatgatttc acgcgatgtt tcagaataca      1080
tgattactaa ggaagagatt tccttgaaag agcttgattt taaattgaga aaacaactta      1140
ttgaaaaaca taatctttac ggtaacatgg gttcaggaac aatcgttatt aaaatgaaaa      1200
acggtgggaa atatacgttt gaattacaca aaaaactgca agagcatcgt atggcagacg      1260
tcatagatgg cactaatatt gataacattg aagtgaatat aaaataatca tgacattctc      1320
taaatagaag ctgtcatcgg aaaaacaaga agttaagtga caacggttta catgttgctt      1380
agcttctttt attatgcgta atgatgtaaa aagacgaata ttcatttgtt tgtaaaagtg      1440
gcatttctat gtcttaaaag tgacgaaact tcaaatgtgc caagtgttga atcacatcaa      1500
aatcattttt atttaacgaa cattatggat ttcttaattt acttaacgat gattcaaata      1560
tagttaaaca aggtttaatg tgaatggagc aatacgccat ctataataaa gctgtatgat      1620
tcaatgaatg taatcgaaca aatctaataa ttacgaatgg agcatacaac tatgaaaata      1680
acaacgattg ctaaaacaag tttagcacta ggccttttaa caacaggtgt aatcacaacg      1740
```

| | |
|---|---|
| acaacgcaag cagcaaacgc gacaacacta tcttccacta aagtggaagc accacaatca | 1800 |
| acaccgccct caactaaaat agaagcaccg caatcaaaac caaacgcgac aacaccgccc | 1860 |
| tcaactaaag tagaagcacc gcaacaaaca gcaaatgcga caacaccgcc ttcaactaaa | 1920 |
| gtgacaacac ctccatcaac aaacacgcca caaccaatgc aatctactaa atcagacaca | 1980 |
| ccacaatcgc caaccacaaa acaagtacca acagaaataa atcctaaatt taaagattta | 2040 |
| agagcgtatt atacgaaacc aagtttagaa tttaaaaatg agattggtat tattttaaaa | 2100 |
| aaatggacga caataagatt tatgaatgtt gtcccagatt atttcatata taaaattgct | 2160 |
| ttagttggta aagatgataa aaaatatggt gaaggagtac ataggaatgt cgatgtattt | 2220 |
| gtcgttttag aagaaaataa ttacaatctg gaaaaatatt ctgtcggtgg tatcacaaag | 2280 |
| agtaatagta aaaaagttga tcacaaagca ggagtaagaa ttactaagga agataataaa | 2340 |
| ggtacaatct ctcatgatgt ttcagaattc aagattacta agaacagat ttccttgaaa | 2400 |
| gaacttgatt ttaaattgag aaaacaactt attgaaaaaa ataatctgta cggtaacgtt | 2460 |
| ggttcaggta aaattgttat taaaatgaaa aacggtggaa agtacacgtt tgaattgcac | 2520 |
| aaaaaattac aagaaaatcg catggcagat gtcatagatg gcactaatat tgataacatt | 2580 |
| gaagtgaata taaaataatc atgacattct ctaaatagaa gctgtcatcg gaaaaacaag | 2640 |
| aagttaagtg acaacggcct acatgttgct tagcttcttt tgttatgttc gatgatttga | 2700 |
| gaacccgaat tttcgatggg tccaaatatg acgtggaaga gacctgaatt tatctgtaaa | 2760 |
| tccctatcta tcgggtgtga agcacaacgg gatc | 2794 |

<210> SEQ ID NO 9
<211> LENGTH: 505
<212> TYPE: DNA
<213> ORGANISM: Staphylococcus aureus

<400> SEQUENCE: 9

| | |
|---|---|
| gatcatagcg caccaaactc tcgtccaatt gattttgaaa tgaaaagaa agatggaact | 60 |
| caacagtttt atcattatgc aagttctgtt aaacctgcta gagttatttt cactgattca | 120 |
| aaaccagaaa ttgaattagg attacaatca ggtcaatttt ggagaaaatt tgaagtttat | 180 |
| gaaggtgaca aaaagttgcc aattaaatta gtatcatacg atactgttaa agattatgct | 240 |
| tacattcgct tctctgtatc aaacggaaca aaagctgtta aaattgttag ttcaacacac | 300 |
| ttcaataaca aagaagaaaa atacgattac acattaatgg aattcgcaca accaatttat | 360 |
| aacagtgcag ataaattcaa aactgaagaa gattataaag ctgaaaaatt attagcgcca | 420 |
| tataaaaaag cgaaaacact agaaagacaa gtttatgaat taaataaaat tcaagataaa | 480 |
| cttcctgaaa aattaaaggc tgagt | 505 |

<210> SEQ ID NO 10
<211> LENGTH: 673
<212> TYPE: DNA
<213> ORGANISM: Staphylococcus aureus

<400> SEQUENCE: 10

| | |
|---|---|
| gatcaaacta aaacacaaac tgctcataca gttaaaacag cacaaactgc tcaagaacaa | 60 |
| aataaagttc aaacacctgt taagatgtt gcaacagcga atctgaaag caacaatcaa | 120 |
| gctgtaagtg ataataaatc acaacaaact aacaaagtta caaaacataa cgaaacgcct | 180 |
| aaacaagcat ctaaagctaa agaattacca aaaactggtt taacttcagt tgataacttt | 240 |
| attagcacag ttgccttcgc aacacttgcc ctttaggtt cattatcttt attacttttc | 300 |

| | |
|---|---:|
| aaaagaaaag aatctaaata aatcatcgtc acactcataa cttaatatat tttttatttt | 360 |
| aaattttatt taacctatgt catagatatt tcataatcta taacataggt tatttttttt | 420 |
| ataaaataac gttgcaatta actaacattt caatgtcaat acaagtaatc aattgataat | 480 |
| gattatcagt tgataatata caattaggag ttgtttctac aacatgaaca aacagcaaaa | 540 |
| agaatttaaa tcattttatt caattagaaa gtcatcacta ggcgtgcatc tgtagcaatt | 600 |
| agtacacttt tattattaat gtcaaatggc gaagcacaag ccagcagctt gaagaaaaca | 660 |
| ggtggtccaa ttc | 673 |

<210> SEQ ID NO 11
<211> LENGTH: 2238
<212> TYPE: DNA
<213> ORGANISM: Staphylococcus aureus

<400> SEQUENCE: 11

| | |
|---|---:|
| gatcttcagc ttgatgtttt cgtttgatta aattggtaaa atagaaacgc aatccacaaa | 60 |
| aatggcaagc actaaaataa tgtttggggg tgcttgtgct tttgtggatt gcggtcgatt | 120 |
| atttatattg catgatttga ttaatttgat tgattatatt ggacatgatg gtgttggcgg | 180 |
| gatgcgttgt tgctagtcgc gggctttgtc cactccacat atgtattaac tctttgtcgc | 240 |
| cgatgtttgc tgcggctttt cttatgctac ttgttagctc attttgtatt ggataatctg | 300 |
| ggatatcgcc ttcgtattgg acatttctt cgataaacct attgttgata ccgcgtgcaa | 360 |
| gctttccact aaacgctttt gtaatgactg tatctgtttc tttactattt ataattgcat | 420 |
| ctcgcagtag ttctgatgca ttactgtctt gtgatgttaa aaatgcggtg cccatttgta | 480 |
| ccccttctgc acctaagaca atacttgcca aaactcctct accatccata attccaccag | 540 |
| cggcaatgac cggaattgaa acgacatcta caatttgtgg cactaaagat attgttccaa | 600 |
| ccataggtaa ttgattttta ggttttaaaa atgaaccacg atgtccacct gcttcactac | 660 |
| cttgagcaac gatagcatcc atacccgctt tttcattcgc aatagcttca tcaacacttg | 720 |
| ttgctgtacc tataagtttg acattcgctg cttttcaacct gcttataatc tgttcgcttg | 780 |
| gaattccaaa agtaaaacaa catacaggca cttgctttt aattatcgta tcaatatgac | 840 |
| acttaaattg ttgttcttcg gtaattttta caaccggctc ttctaaatgt aatgcgcgtc | 900 |
| gataaggttt taaccatgca ttcatatttt caatttgact actggtatat gattgttgac | 960 |
| ttggtacaaa gacatttacg ccaaaagaat ttgacgttaa ttggcgtaca taatctattt | 1020 |
| catcttccaa ttgctgcgta ttaaagtaac ctgcgcctat tgtgcctaac ccaccactgt | 1080 |
| tacttactga tgcaactaat ttcggtgtcg tacttcctgc catacctgct tgtataattg | 1140 |
| gatattcaat acttaacatt tgagtaagtc gattcttatt ccacatagct gttcgctcct | 1200 |
| tatatagata cgttgcgatt tttccgttgt tgaaattgaa tttgctgttg agaaagtttt | 1260 |
| tcttttcct tttatccat ctcatcttca atttccatac ctaataattc ttcaattaag | 1320 |
| tcttcatgtg acactatcgc ttcagtacca ccaaattcgt ccaacacaat gctaaatgt | 1380 |
| tttctagaaa tagtcatctt acgtaatacc cattcagctt tattgtgttc attcacaaat | 1440 |
| aatggcttag ctgaatagtt tgtaatttga ttttctttt tattactcca agccaacaga | 1500 |
| tatttagaat gaaacacccc aataatgtta tcaatatctc cctcgtacac tggatatcta | 1560 |
| gtgtatggct tattcataac cgtttcataa acttcttcgt atgtcgcatt tgaagcaaat | 1620 |
| gccgtcacat taattctagg tgttgtatct acatcttta cttttaaatt ttcaaaatta | 1680 |
| atgacacctt ccaacctact cgtctcaatt tcatttaaag caccttcatg tccagcaatt | 1740 |

-continued

```
gctaacattg ttttaaattc ttcttttgaa aattgatgtt cttgaggttg gcccttagat    1800
aaacttcgat taatactgtc cgtcaactta tttaaaagta atgtgatagg acggaacaca    1860
atgacacaaa tattaataat tggatataca agccttgtta ttttatctgg aaatgttgca    1920
gcgacagact tgggaatcac ttcggagatc aaaatgataa caactgttaa aacagctgat    1980
gcaataccaa cgctaatccc ccaacgtaaa gccataattg taacaagtgt tggtaataaa    2040
atattcgcga cattattccc aattagaatc gttgtaataa actcacttgg tttttcaagt    2100
aactttacaa tgccttttgc ttttttatca cctttgtcag cttcagtttt aaattttgct    2160
ttattggcag ccgttaatgc cgtctcgctt cctgaaaaga aaacgaaat aaatatcaat    2220 ataattatgg caatgatc                                                 2238

<210> SEQ ID NO 12
<211> LENGTH: 7975
<212> TYPE: DNA
<213> ORGANISM: Staphylococcus aureus

<400> SEQUENCE: 12
gatcaaacga caattattaa ttcgttaacg tttactgaaa cagtaccaaa tagaagttat      60
gcaagagcaa gtgcgaatga atcactagt aaaacagtta gtaatgtcag tcgtactgga     120
aataatgcca atgtcacagt aactgttact tatcaagatg gaacaacatc aacagtgact     180
gtacctgtaa agcatgtcat tccagaaatc gttgcacatt cgcattacac tgtacaaggc     240
caagacttcc cagcaggtaa tggttctagt gcatcagatt actttaagtt atctaatggt     300
agtgacattg cagatgcaac tattacatgg gtaagtggac aagcgccaaa taagataat     360 acacgtattg gtgaagatat aactgtaact gcacatatct taattgatgg cgaaacaacg     420
ccgattacga aaacagcaac atataaagta gtaagaactg taccgaaaca tgtctttgaa     480
acagccagag gtgttttata cccaggtgtt tcagatatgt atgatgcgaa acaatatgtt     540
aagccagtaa ataattcttg gtcgacaaat gcgcaacata tgaatttcca atttgttgga     600
acatatggtc ctaacaaaga tgttgtaggc atatctactc gtcttattag agtgacatat     660
gataatagac aaacagaaga tttaactatt ttatctaaag ttaaacctga cccacctaga     720
attgacgcaa actctgtgac atataaagca ggtcttacaa accaagaaat taagttaat     780 aacgtattaa ataactcgtc agtaaaatta tttaaagcag ataatacacc attaaatgtc     840
acaaatatta ctcatggtag cggttttagt tcggttgtga cagtaagtga cgcgttacca     900
aatggcggaa ttaaagcaaa atcttcaatt tcaatgaaca atgtgacgta tacgacgcaa     960
gacgaacatg gtcaagttgt tacagtaaca agaaatgaat ctgttgattc aaatgacagt    1020
gcaacagtaa cagtgacacc acaattacaa gcaactactg aaggcgctgt atttattaaa    1080
ggtggcgacg ttttgatt cggacacgta gaaagattta ttcaaaaccc gccacatggg    1140
gcaacggttg catggcatga tagtccagat acatggaaga atacagtcgg taacactcat    1200
aaaactgcgg ttgtaacatt acctaatggt caaggtacgc gtaatgttga agttccagtc    1260
aaagtttatc cagttgctaa tgcaaaggcg ccatcacgtg atgtgaaagg tcaaaatttg    1320
actaatggaa cggatgcgat gaactacatt acatttgatc caaatacaaa cacaaatggt    1380
atcactgcag catgggcaaa tagacaacaa ccaataaacc aacaagcagg cgtgcaacat    1440
ttaaatgtcg atgtcacata tccaggtatt tcagctgcta aacgagttcc tgttactgtt    1500
aatgtatatc aattttgaatt ccctcaaact acttatacga caacggttgg aggcacttta    1560
gcaagtggta cgcaagcatc aggatatgca catatgcaaa atgctactgg tttaccaaca    1620
```

```
gatggattta cgtataaatg gaatcgtgat actacaggta caaatgacgc aaactggtca   1680
gctatgaata aaccgaatgt ggctaaagtc gttaacgcaa atatgacgt catctataac    1740 ggacatactt ttgcaacatc tttaccagcg aaatttgtag taaaagatgt gcaaccagcg   1800
aaaccaactg tgactgaaac agcggcagga gcgattacaa ttgcacctgg agcaaaccaa   1860
acagtgaata cacatgccgg taacgtaacg acatacgctg ataaattagt tattaaacgt   1920
aatggtaacg ttgtgacgac atttacacgt cgcaataata cgagtccatg ggtgaaagaa   1980
gcatctgcag caactgtagc aggtattgct ggaactaata atggtattac tgttgcagca   2040
ggtactttca acccctgctga tacaattcaa gttgttgcaa cgcaaggaag cggagagaca   2100
gtgagtgatg agcaacgtag tgatgatttc acagttgtcg caccacaacc gaaccaagcg   2160
actactaaga tttggcaaaa tggtcatatt gatatcacgc ctaataatcc atcaggacat   2220
ttaattaatc caactcaagc aatggatatt gcttacactg aaaaagtggg taatggtgca   2280
gaacatagta agacaattaa tgttgttcgt ggtcaaaata tcaatggac  aattgcgaat   2340 aagcctgact atgtaacgtt agatgcacaa actggtaaag tgacgttcaa tgccaatact   2400
ataaaaccaa attcatcaat cacaattact ccgaaagcag gtacaggtca ctcagtaagt   2460
agtaatccaa gtacattaac tgcaccggca gctcatactg tcaacacaac tgaaattgtg   2520
aaagattatg gttcaaatgt aacagcagct gaaattaaca atgcagttca agttgctaat   2580
aaacgtactg caacgattaa aaatggcaca gcaatgccta ctaatttagc tggtggtagc   2640
acaacgacga ttcctgtgac agtaacttac aatgatggta gtactgaaga agtacaagag   2700 tccatttca  caaaagcgga taaacgtgag ttaatcacag ctaaaaatca tttagatgat   2760
ccagtaagca ctgaaggtaa aaagccaggt acaattacgc agtacaataa tgcaatgcat   2820
aatgcgcaac aacaaatcaa tactgcgaaa acagaagcac aacaagtgat taataatgag   2880
cgtgcaacac cacaacaagt ttctgacgca ctaactaaag ttcgtgcagc acaaactaag   2940
attgatcaag ctaaagcatt acttcaaaat aaagaagata atagccaatt agtaacgtct   3000
aaaaataact acaaagttc  tgtgaaccaa gtaccatcaa ctgctggtat gacgcaacaa   3060
agtattgata actataatgc gaagaagcgt gaagcagaaa ctgaaataac tgcagctcaa   3120
cgtgttattg acaatggcga tgcaactgca caacaaattt cagatgaaaa acatcgtgtc   3180
gataacgcat taacagcatt aaaccaagcg aaacatgatt taactgcaga tacacatgcc   3240
ttagagcaag cagtgcaaca attgaatcgc acaggtacaa cgactggtaa gaagccggca   3300
agtattactg cttacaataa ttcgattcgt gcacttcaaa gtgacttaac aagtgctaaa   3360
aatagcgcta atgctattat tcaaaagcca ataagaacag tacaagaagt gcaatctgcg   3420
ttaacaaatg taaatcgtgt caatgagcga ttaacgcaag caattaatca attagtacct   3480
ttagctgata atagtgcttt aaaaactgct aagacgaaac ttgatgaaga aatcaataaa   3540
tcagtaacta ctgatggtat gacacaatca tcaatccaag catatgaaaa tgctaaacgt   3600
gcgggtcaaa cagaatcaac aaatgcacaa aatgttatta acaatggtga tgcgactgac   3660
caacaaattg ccgcagaaaa aacaaaagta gaagaaaaat ataatagctt aaaacaagca   3720
attgctggat taactccaga cttggcacca ttacaaactg caaaaactca gttgcaaaat   3780
gatattgatc agccaacgag tacgactggt atgacaagcg catctattgc agcatttaat   3840
gaaaaacttt cagcagctag aactaaaatt caagaaattg atcgtgtatt agcctcacat   3900
ccagatgttg cgacaatacg tcaaaacgtg acagcagcga atgccgctaa atcagcactt   3960
gatcaagcac gtaatggctt aacagtcgat aaagcgcctt tagaaaatgc gaaaaatcaa   4020
```

```
ctacaatata gtattgacac gcaaacaagt acaactggta tgacacaaga ctctataaat    4080
gcatacaatg cgaagttaac agctgcacgt aataagattc aacaaatcaa tcaagtatta    4140
gcaggttcac cgactgtaga acaaattaat acaaatacgt ctacagcaaa tcaagctaaa    4200
tctgatttag atcatgcacg tcaagcttta acaccagata aagcgccgct tcaaactgcg    4260
aaaacgcaat tagaacaaag cattaatcaa ccaacggata caacaggtat gacgaccgct    4320
tcgttaaatg cgtacaacca aaaattacaa gcagcgcgtc aaaagttaac tgaaattaat    4380
caagtgttga atggcaaccc aactgtccaa aatatcaatg ataaagtgac agaggcaaac    4440
caagctaagg atcaattaaa tacagcacgt caaggtttaa cattagatag acagccagcg    4500
ttaacaacat tacatggtgc atctaactta aaccaagcac aacaaaataa tttcacgcaa    4560
caaattaatg ctgctcaaaa tcatgctgcg cttgaaacaa ttaagtctaa cattacggct    4620
ttaaatactg cgatgacgaa attaaaagac agtgttgcgg ataataatac aattaaatca    4680
gatcaaaatt acactgacgc aacaccagct aataaacaag cgtatgataa tgcagttaat    4740
gcggctaaag gtgtcattgg agaaacgact aatccaacga tggatgttaa cacagtgaac    4800
caaaaagcag catctgttaa atcgacgaaa gatgctttag atggtcaaca aaacttacaa    4860
cgtgcgaaaa cagaagcaac aaatgcgatt acgcatgcaa gtgatttaaa ccaagcacaa    4920
aagaatgcat taacacaaca agtgaatagt gcacaaaacg tgcaagcagt aaatgatatt    4980
aaacaaacga ctcaaagctt aaatactgct atgacaggtt taaaacgtgg cgttgctaat    5040
cataaccaag tcgtacaaag tgataattat gtcaacgcag atactaataa gaaaaatgat    5100
tacaacaatg catacaacca tgcgaatgac attattaatg gtaatgcaca acatccagtt    5160
ataacaccaa gtgatgttaa caatgctttta tcaaatgtca caagtaaaga acatgcattg    5220
aatggtgaag ctaagttaaa tgctgcgaaa caagaagcga atactgcatt aggtcattta    5280
aacaatttaa ataatgcaca acgtcaaaac ttacaatcgc aaattaatgg tgcgcatcaa    5340
attgatgcag ttaatacaat taagcaaaat gcaacaaact tgaatagtgc aatgggtaac    5400
ttaagacaag ctgttgcaga taaagatcaa gtgaaacgta cagaagatta tgcggatgca    5460
gatacagcta aacaaaatgc atataacagt gcagtttcaa gtgccgaaac aatcattaat    5520
caaacaacaa atccaacgat gtctgttgat gatgttaatc gtgcaacttc agctgttact    5580
tctaataaaa atgcattaaa tggttatgaa aaattagcac aatctaaaac agatgctgca    5640
agagcaattg atgcattacc acatttaaat aatgcacaaa aagcagatgt taaatctaaa    5700
attaatgctg catcaaatat tgctggcgta aatactgtta acaacaagg tacagattta    5760
aatacagcga tgggtaactt gcaaggtgca atcaatgatg aacaaacgac gcttaatagt    5820
caaaactatc aagatgcgac acctagtaag aaaacagcat acacaaatgc ggtacaagct    5880
gcgaaagata tttttaaataa atcaaatggt caaataaaa cgaaagatca agttactgaa    5940
gcgatgaatc aagtgaattc tgctaaaaat aacttagatg gtacgcgttt attagatcaa    6000
gcgaagcaaa cagcaaaaca gcagttaaat aatatgacgc atttaacaac tgcacaaaaa    6060
acgaatttaa caaaccaaat taatagtggt actactgtcg ctggtgttca aacggttcaa    6120
tcaaatgcca atacattaga tcaagccatg aatacgttaa gacaaagtat tgccaacaaa    6180
gatgcgacta aagcaagtga agattacgta gatgctaata atgataagca aacagcatat    6240
aacaacgcag tagctgctgc tgaaacgatt attaatgcta atagtaatcc agaaatgaat    6300
ccaagtacga ttcacaaaaa agcagagcaa gtgaatagtt ctaaaacggc acttaacggt    6360
gatgaaaact tagctgctgc aaaacaaaat gcgaaaacgt acttaaacac attgacaagt    6420
```

-continued

```
attacagatg ctcaaaagaa caatttgatt agtcaaatta ctagtgcgac aagagtgagt    6480
ggtgttgata ctgtaaaaca aaatgcgcaa catctagacc aagctatggc tagcttacag    6540
aatggtatta acaacgaatc tcaagtgaaa tcatctgaga atatcgtga tgctgataca     6600 aataaacaac aagagtatga taatgctatt actgcagcga aagcgatttt aaataaatcg    6660
acaggtccaa acactgcgca aatgcagtt gaagcagcat tacaacgtgt taataatgcg     6720
aaagatgcat tgaatggtga tgcaaaatta attgcagctc aaaacgcagc gaaacaacat    6780
ttaggtactt taacgcatat cactacagct caacgtaatg atttaacaaa tcaaatttca    6840
caagctacaa acttagctgg tgttgaatct gttaaacaaa atgcgaatag tttagatggt    6900
gctatgggta acttacaaac ggctatcaac gataagtcag gaacattagc gagccaaaac    6960
ttcttggatc tgatgagca aaaacgtaat gcatacaatc aagctgtatc agcagccgaa     7020
accattttaa ataaacaaac tggaccgaat acagcgaaaa cagcagtcga caagcactt    7080 aataatgtta ataatgcgaa acatgcatta aatggtacgc aaaacttaaa caatgcgaaa    7140
caagcagcga ttacagcaat caatggcgca tctgatttaa atcaaaaaca aaaagatgca    7200
ttaaaagcac aagctaatgg tgctcaacgc gtatctaatg cacaagatgt acagcacaat    7260
gcgactgaac tgaacacggc aatgggcaca ttaaaacatg ccatcgcaga taagacgaat    7320
acgttagcaa gcagtaaata tgttaatgcc gatagcacta acaaaatgc ttacacaact    7380 aaagttacca atgctgaaca tattattagc ggtacgccaa cggttgttac gacaccttca    7440
gaagtaacag ctgcagctaa tcaagtaaac agcgcgaaac aagaattaaa tggtgacgaa    7500
agattacgtg aagcaaaaca aaacgccaat actgctattg atgcattaac acaattaaat    7560
acacctcaaa aagctaaatt aaaagaacaa gtgggacaag ccaatagatt agaagacgta    7620
caaactgttc aaacaaatgg acaagcattg aacaatgcaa tgaaaggctt aagagatagt    7680
attgctaacg aaacaacagt caaaacaagt caaaactata cagacgcaag tccgaataac    7740
caatcaacat ataatagcgc tgtgtcaaat gcgaaaggta tcattaatca aactaacaat    7800
ccgactatgg atactagtgc gattacccaa gctacaacac aagtgaataa tgctaaaaat    7860
ggtttaaacg gtgctgaaaa cttaagaaat gcacaaaaca ctgctaagca aaacttaaat    7920
acattatcac acttaacaaa taaccaaaaa tctgccatct catcacaaat tgatc         7975
```

<210> SEQ ID NO 13
<211> LENGTH: 2001
<212> TYPE: DNA
<213> ORGANISM: Staphylococcus aureus

<400> SEQUENCE: 13

```
gatcatggca ttgtatttaa tgcaagtcta cctttgtaca aagatgccat ccatcaaaaa      60
ggatcaatgc gcagtaatga caatggtgat gatatgagta tgatggtggg tacagtgctg    120
agtggctttg aatatcgagc gcaaaaagaa agtatgata acttatataa attcttcaaa     180
gaaaatgaaa agaaatatca atatacaggc tttacaaaag aggcaattaa caagacacaa    240
aatgtcggat ataaaaatga atatttttat attacatact cttctagaag tttaaaagaa    300
tatcgaaagt attatgaacc actgattcga aaaaatgata agaatttaa agaaggaatg     360 gaacgagcaa gaaagaagt gaattacgct gcaaatacag atgctgttgc tacactttt     420 tctactaaga aaactttac taaagacaat acagtagatg atgtaatcga actaagtgat    480
aaattatata atttaaaaaa taaccagat aaatctacaa tcacaataca aatagggaaa    540
cccactatta atactaagaa agcctttat gatgataatc gtccaataga atatggggtg    600
```

-continued

```
cacagtaaag atgaataaaa ttaatgatag ggatttaaca gaattaagta gttactgggt      660
ttatcaaaat attgatataa aaaagaatt taaagttaat ggaaaaaggt ttaaacaagt       720
agacagttat aatgatgata agaatagtaa tttgaatggt gctgctgata ttaaaatata      780
tgagttatta gatgataaaa gtaaaccaac tggtcaacag acaataattt atcaaggaac      840
atctaatgag gcaattaatc caaataatcc attaaaatca tcggggtttg gagatgattg      900
gctccaaaat gctaaattaa tgaataatga taatgaaagc acagattatt taaagcaaac      960
agatcaatta tcaaatcaat ataaaataaa gttagaagat gcagatagat tatcaaatag     1020
tgattttta aaaaaatata gaatggaatc aagtaacttc aaaaacaaaa ccattgtggc      1080
ggatggcggt aattcggaag gcggtgcagg agcaaaatat caaggagcga acatccgaa      1140
tgaaaaagtt gttgctactg actcagcaat gattccttat gctgcttggc agaaatttgc     1200
tagaccacgc tttgataata tgattagttt taatagtacc aacgatttat taacatggtt     1260
acaagatcca ttcatcaaag atatgccagg aaaacgcgtt aacattaatg atggtgtgcc     1320
caggttagat actttaatag acagccatgt aggttataaa aggaagttaa atagaaaaga    1380
taacacatac gatactgtac cactaatcaa aataaagtcg gtaaaagata cagaaattaa     1440
aaatggaaaa aaagtaaaaa agactattaa cataacatta gatatggatg gcgaattcc     1500
aataaatgtt tggacaggag attcgattgc acgttctgga agaggaactt taattaaact     1560
taatttagaa aatcttgatg cgttgagtaa actgattact ggtgaaacaa gtggtatgtt    1620
agcagaatgc gtaatctttt taaatgaaag ttttaacatc tcagaaaatg aaaataaaaa     1680
ttttgcagat agaaagaaac aattatcaga aggatttaag gataagatta acttatttca    1740
gttagaagaa atggaaagaa ctttaattag taaaataaac tcacttgaag aagttgcaga    1800
tgaaacaata gaaagtatta gtgctgttaa acacttatta cctgattttg cattggatgc    1860
attaaaagaa agaattaatg agttgtttaa aggtataaaa tcttttatag aaaagtgta     1920
tgatagtata gataatgaaa ttttagaaat tttcaaaaat atagatcacg acttcagaga    1980
tggagtatct gaagaaatga t                                              2001
```

<210> SEQ ID NO 14
<211> LENGTH: 106
<212> TYPE: PRT
<213> ORGANISM: Staphylococcus aureus

<400> SEQUENCE: 14

```
Asp Gln Thr Lys Thr Gln Thr Ala His Thr Val Lys Thr Ala Gln Thr
  1               5                  10                  15

Ala Gln Glu Gln Asn Lys Val Gln Thr Pro Val Lys Asp Val Ala Thr
             20                  25                  30

Ala Lys Ser Glu Ser Asn Asn Gln Ala Val Ser Asp Asn Lys Ser Gln
         35                  40                  45

Gln Thr Asn Lys Val Thr Lys His Asn Glu Thr Pro Lys Gln Ala Ser
     50                  55                  60

Lys Ala Lys Glu Leu Pro Lys Thr Gly Leu Thr Ser Val Asp Asn Phe
 65                  70                  75                  80

Ile Ser Thr Val Ala Phe Ala Thr Leu Ala Leu Gly Ser Leu Ser
                 85                  90                  95

Leu Leu Leu Phe Lys Arg Lys Glu Ser Lys
            100                 105
```

<210> SEQ ID NO 15
<211> LENGTH: 960
<212> TYPE: PRT
<213> ORGANISM: Staphylococcus aureus

<400> SEQUENCE: 15

```
Asp Arg Ile Ile Glu Thr Ala Pro Thr Asp Tyr Leu Ser Trp Gly Val
  1               5                  10                  15

Gly Ala Val Gly Asn Pro Arg Phe Ile Asn Val Glu Ile Val His Thr
             20                  25                  30

His Asp Tyr Ala Ser Phe Ala Arg Ser Met Asn Asn Tyr Ala Asp Tyr
         35                  40                  45

Ala Ala Thr Gln Leu Gln Tyr Tyr Gly Leu Lys Pro Asp Ser Ala Glu
     50                  55                  60

Tyr Asp Gly Asn Gly Thr Val Trp Thr His Tyr Ala Val Ser Lys Tyr
 65                  70                  75                  80

Leu Gly Gly Thr Asp His Ala Asp Pro His Gly Tyr Leu Arg Ser His
                 85                  90                  95

Asn Tyr Ser Tyr Asp Gln Leu Tyr Asp Leu Ile Asn Glu Lys Tyr Leu
            100                 105                 110

Ile Lys Met Gly Lys Val Ala Pro Trp Gly Thr Gln Ser Thr Thr Thr
        115                 120                 125

Pro Thr Thr Pro Ser Lys Pro Thr Thr Pro Ser Lys Pro Ser Thr Gly
    130                 135                 140

Lys Leu Thr Val Ala Ala Asn Asn Gly Val Ala Gln Ile Lys Pro Thr
145                 150                 155                 160

Asn Ser Gly Leu Tyr Thr Thr Val Tyr Asp Lys Thr Gly Lys Ala Thr
                165                 170                 175

Asn Glu Val Gln Lys Thr Phe Ala Val Ser Lys Thr Ala Thr Leu Gly
            180                 185                 190

Asn Gln Lys Phe Tyr Leu Val Gln Asp Tyr Asn Ser Gly Asn Lys Phe
        195                 200                 205

Gly Trp Val Lys Glu Gly Asp Val Val Tyr Asn Thr Ala Lys Ser Pro
    210                 215                 220

Val Asn Val Asn Gln Ser Tyr Ser Ile Lys Pro Gly Thr Lys Leu Tyr
225                 230                 235                 240

Thr Val Pro Trp Gly Thr Ser Lys Gln Val Ala Gly Ser Val Ser Gly
                245                 250                 255

Ser Gly Asn Gln Thr Phe Lys Ala Ser Lys Gln Gln Ile Asp Lys
            260                 265                 270

Ser Ile Tyr Leu Tyr Gly Ser Val Asn Gly Lys Ser Gly Trp Val Ser
        275                 280                 285

Lys Ala Tyr Leu Val Asp Thr Ala Lys Pro Thr Pro Thr Pro Thr Pro
    290                 295                 300

Lys Pro Ser Thr Pro Thr Thr Asn Asn Lys Leu Thr Val Ser Ser Leu
305                 310                 315                 320

Asn Gly Val Ala Gln Ile Asn Ala Lys Asn Asn Gly Leu Phe Thr Thr
                325                 330                 335

Val Tyr Asp Lys Thr Gly Lys Pro Thr Lys Glu Val Gln Lys Thr Phe
            340                 345                 350

Ala Val Thr Lys Glu Ala Ser Leu Gly Gly Asn Lys Phe Tyr Leu Val
        355                 360                 365

Lys Asp Tyr Asn Ser Pro Thr Leu Ile Gly Trp Val Lys Gln Gly Asp
    370                 375                 380
```

```
Val Ile Tyr Asn Asn Ala Lys Ser Pro Val Asn Val Met Gln Thr Tyr
385                 390                 395                 400

Thr Val Lys Pro Gly Thr Lys Leu Tyr Ser Val Pro Trp Gly Thr Tyr
            405                 410                 415

Lys Gln Glu Ala Gly Ala Val Ser Gly Thr Gly Asn Gln Thr Phe Lys
            420                 425                 430

Ala Thr Lys Gln Gln Gln Ile Asp Lys Ser Ile Tyr Leu Phe Gly Thr
        435                 440                 445

Val Asn Gly Lys Ser Gly Trp Val Ser Lys Ala Tyr Leu Ala Val Pro
    450                 455                 460

Ala Ala Pro Lys Lys Ala Val Ala Gln Pro Lys Thr Ala Val Lys Ala
465                 470                 475                 480

Tyr Thr Val Thr Lys Pro Gln Thr Thr Gln Thr Val Ser Lys Ile Ala
                485                 490                 495

Gln Val Lys Pro Asn Asn Thr Gly Ile Arg Ala Ser Val Tyr Glu Lys
            500                 505                 510

Thr Ala Lys Asn Gly Ala Lys Tyr Ala Asp Arg Thr Phe Tyr Val Thr
        515                 520                 525

Lys Glu Arg Ala His Gly Asn Glu Thr Tyr Val Leu Leu Asn Asn Thr
    530                 535                 540

Ser His Asn Ile Pro Leu Gly Trp Phe Asn Val Lys Asp Leu Asn Val
545                 550                 555                 560

Gln Asn Leu Gly Lys Glu Val Lys Thr Thr Gln Lys Tyr Thr Val Asn
                565                 570                 575

Lys Ser Asn Asn Gly Leu Ser Met Val Pro Trp Gly Thr Lys Asn Gln
            580                 585                 590

Val Ile Leu Thr Gly Asn Asn Ile Ala Gln Gly Thr Phe Asn Ala Thr
        595                 600                 605

Lys Gln Val Ser Val Gly Lys Asp Val Tyr Leu Tyr Gly Thr Ile Asn
    610                 615                 620

Asn Arg Thr Gly Trp Val Asn Ala Lys Asp Leu Thr Ala Pro Thr Ala
625                 630                 635                 640

Val Lys Pro Thr Thr Ser Ala Ala Lys Asp Tyr Asn Tyr Thr Tyr Val
                645                 650                 655

Ile Lys Asn Gly Asn Gly Tyr Tyr Tyr Val Thr Pro Asn Ser Asp Thr
            660                 665                 670

Ala Lys Tyr Ser Leu Lys Ala Phe Asn Glu Gln Pro Phe Ala Val Val
        675                 680                 685

Lys Glu Gln Val Ile Asn Gly Gln Thr Trp Tyr Tyr Gly Lys Leu Ser
    690                 695                 700

Asn Gly Lys Leu Ala Trp Ile Lys Ser Thr Asp Leu Ala Lys Glu Leu
705                 710                 715                 720

Ile Lys Tyr Asn Gln Thr Gly Met Ala Leu Asn Gln Val Ala Gln Ile
            725                 730                 735

Gln Ala Gly Leu Gln Tyr Lys Pro Gln Val Gln Arg Val Pro Gly Lys
        740                 745                 750

Trp Thr Gly Ala Asn Phe Asn Asp Val Lys His Ala Met Asp Thr Lys
    755                 760                 765

Arg Leu Ala Gln Asp Pro Ala Leu Lys Tyr Gln Phe Leu Arg Leu Asp
    770                 775                 780

Gln Pro Gln Asn Ile Ser Ile Asp Lys Ile Asn Gln Phe Leu Lys Gly
785                 790                 795                 800
```

```
Lys Gly Val Leu Glu Asn Gln Gly Ala Ala Phe Asn Lys Ala Ala Gln
                805                 810                 815
Met Tyr Gly Ile Asn Glu Val Tyr Leu Ile Ser His Ala Leu Leu Glu
            820                 825                 830
Thr Gly Asn Gly Thr Ser Gln Leu Ala Lys Gly Ala Asp Val Val Asn
        835                 840                 845
Asn Lys Val Val Thr Asn Ser Asn Thr Lys Tyr His Asn Val Phe Gly
    850                 855                 860
Ile Ala Ala Tyr Asp Asn Asp Pro Leu Arg Glu Gly Ile Lys Tyr Ala
865                 870                 875                 880
Lys Gln Ala Gly Trp Asp Thr Val Ser Lys Ala Ile Val Gly Gly Ala
                885                 890                 895
Lys Phe Ile Gly Asn Ser Tyr Val Lys Ala Gly Gln Asn Thr Leu Tyr
            900                 905                 910
Lys Met Arg Trp Asn Pro Ala His Pro Gly Thr His Gln Tyr Ala Thr
        915                 920                 925
Asp Val Asp Trp Ala Asn Ile Asn Ala Lys Ile Ile Lys Gly Tyr Tyr
    930                 935                 940
Asp Lys Ile Gly Glu Val Gly Tyr Phe Asp Ile Pro Gln Tyr Lys
945                 950                 955                 960

<210> SEQ ID NO 16
<211> LENGTH: 386
<212> TYPE: PRT
<213> ORGANISM: Staphylococcus aureus

<400> SEQUENCE: 16

Asp Gln Tyr Ser Glu Asp Ala Lys Lys Thr Gln Lys Asp Tyr Ala Ser
1               5                   10                  15
Gln Ser Lys Lys Asp Lys Asn Glu Lys Ser Asn Thr Lys Asn Pro Gln
                20                  25                  30
Leu Pro Thr Gln Asp Glu Leu Lys His Lys Ser Lys Pro Ala Gln Ser
            35                  40                  45
Phe Asn Asn Asp Val Asn Gln Lys Asp Thr Arg Ala Thr Ser Leu Phe
        50                  55                  60
Glu Thr Asp Pro Ser Ile Ser Asn Asn Asp Asp Ser Gly Gln Phe Asn
65                  70                  75                  80
Val Val Asp Ser Lys Asp Thr Arg Gln Phe Val Lys Ser Ile Ala Lys
                85                  90                  95
Asp Ala His Arg Ile Gly Gln Asp Asn Asp Ile Tyr Ala Ser Val Met
            100                 105                 110
Ile Ala Gln Ala Ile Leu Glu Ser Asp Ser Gly Arg Ser Ala Leu Ala
        115                 120                 125
Lys Ser Pro Asn His Asn Leu Phe Gly Ile Lys Gly Ala Phe Glu Gly
    130                 135                 140
Asn Ser Val Pro Phe Asn Thr Leu Glu Ala Asp Gly Asn Gln Leu Tyr
145                 150                 155                 160
Ser Ile Asn Ala Gly Phe Arg Lys Tyr Pro Ser Thr Lys Glu Ser Leu
                165                 170                 175
Lys Asp Tyr Ser Asp Leu Ile Lys Asn Gly Ile Asp Gly Asn Arg Thr
            180                 185                 190
Ile Tyr Lys Pro Thr Trp Lys Ser Glu Ala Asp Ser Tyr Lys Asp Ala
        195                 200                 205
Thr Ser His Leu Ser Lys Thr Tyr Ala Thr Asp Pro Asn Tyr Ala Lys
    210                 215                 220
```

```
Lys Leu Asn Ser Ile Ile Lys His Tyr Gln Leu Thr Gln Phe Asp Asp
225                 230                 235                 240

Glu Arg Met Pro Asp Leu Asp Lys Tyr Glu Arg Ser Ile Lys Asp Tyr
            245                 250                 255

Asp Asp Ser Ser Asp Glu Phe Lys Pro Phe Arg Glu Val Ser Asp Ser
        260                 265                 270

Met Pro Tyr Pro His Gly Gln Cys Thr Trp Tyr Val Tyr Asn Arg Met
    275                 280                 285

Lys Gln Phe Gly Thr Ser Ile Ser Gly Asp Leu Gly Asp Ala His Asn
290                 295                 300

Trp Asn Asn Arg Ala Gln Tyr Arg Asp Tyr Gln Val Ser His Thr Pro
305                 310                 315                 320

Lys Arg His Ala Ala Val Val Phe Glu Ala Gly Gln Phe Gly Ala Asp
                325                 330                 335

Gln His Tyr Gly His Val Ala Phe Val Glu Lys Val Asn Ser Asp Gly
            340                 345                 350

Ser Ile Val Ile Ser Glu Ser Asn Val Lys Gly Leu Gly Ile Ile Ser
        355                 360                 365

His Arg Thr Ile Asn Ala Ala Ala Ala Glu Glu Leu Ser Tyr Ile Thr
370                 375                 380

Gly Lys
385

<210> SEQ ID NO 17
<211> LENGTH: 325
<212> TYPE: PRT
<213> ORGANISM: Staphylococcus aureus

<400> SEQUENCE: 17

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205
```

```
Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270

Arg Glu Met Asp Leu Tyr Gln Ile Arg Trp Asn Gly Phe Tyr Trp Ala
        275                 280                 285

Gly Ala Asn Tyr Lys Asn Phe Lys Thr Arg Thr Phe Lys Ser Thr Tyr
    290                 295                 300

Glu Ile Asp Trp Glu Asn His Lys Val Lys Leu Leu Asp Thr Lys Glu
305                 310                 315                 320

Thr Glu Asn Asn Lys
                325

<210> SEQ ID NO 18
<211> LENGTH: 157
<212> TYPE: PRT
<213> ORGANISM: Staphylococcus aureus

<400> SEQUENCE: 18

Ser Phe Asn Tyr Ser Lys Ser Ile Ser Tyr Thr Gln Gln Asn Tyr Val
1               5                   10                  15

Ser Glu Val Glu Gln Gln Asn Ser Lys Ser Val Leu Trp Gly Val Lys
            20                  25                  30

Ala Asn Ser Phe Ala Thr Glu Ser Gly Gln Lys Ser Ala Phe Asp Ser
        35                  40                  45

Asp Leu Phe Val Gly Tyr Lys Pro His Ser Lys Asp Pro Arg Asp Tyr
    50                  55                  60

Phe Val Pro Asp Ser Glu Leu Pro Pro Leu Val Gln Ser Gly Phe Asn
65                  70                  75                  80

Pro Ser Phe Ile Ala Thr Val Ser His Glu Lys Gly Ser Ser Asp Thr
                85                  90                  95

Ser Glu Phe Glu Ile Thr Tyr Gly Arg Asn Met Asp Val Thr His Ala
            100                 105                 110

Ile Lys Arg Ser Thr His Tyr Gly Asn Ser Tyr Leu Asp Gly His Arg
        115                 120                 125

Val His Asn Ala Phe Val Asn Arg Asn Tyr Thr Val Lys Tyr Glu Val
    130                 135                 140

Asn Trp Lys Thr His Glu Ile Lys Val Lys Gly Gln Asn
145                 150                 155

<210> SEQ ID NO 19
<211> LENGTH: 345
<212> TYPE: PRT
<213> ORGANISM: Staphylococcus aureus

<400> SEQUENCE: 19

Ile Ile Ala Ile Ile Ile Leu Ile Phe Ile Ser Phe Phe Ser Gly
1               5                   10                  15

Ser Glu Thr Ala Leu Thr Ala Ala Asn Lys Ala Lys Phe Lys Thr Glu
            20                  25                  30

Ala Asp Lys Gly Asp Lys Lys Ala Lys Gly Ile Val Lys Leu Leu Glu
        35                  40                  45
```

```
Lys Pro Ser Glu Phe Ile Thr Thr Ile Leu Ile Gly Asn Asn Val Ala
     50                  55                  60

Asn Ile Leu Leu Pro Thr Leu Val Thr Ile Met Ala Leu Arg Trp Gly
 65                  70                  75                  80

Ile Ser Val Gly Ile Ala Ser Ala Val Leu Thr Val Val Ile Ile Leu
                 85                  90                  95

Ile Ser Glu Val Ile Pro Lys Ser Val Ala Ala Thr Phe Pro Asp Lys
                100                 105                 110

Ile Thr Arg Leu Val Tyr Pro Ile Ile Asn Ile Cys Val Ile Val Phe
            115                 120                 125

Arg Pro Ile Thr Leu Leu Asn Lys Leu Thr Asp Ser Ile Asn Arg
130                 135                 140

Ser Leu Ser Lys Gly Gln Pro Gln Glu His Gln Phe Ser Lys Glu Glu
145                 150                 155                 160

Phe Lys Thr Met Leu Ala Ile Ala Gly His Glu Gly Ala Leu Asn Glu
                165                 170                 175

Ile Glu Thr Ser Arg Leu Glu Gly Val Ile Asn Phe Glu Asn Leu Lys
                180                 185                 190

Val Lys Asp Val Asp Thr Thr Pro Arg Ile Asn Val Thr Ala Phe Ala
            195                 200                 205

Ser Asn Ala Thr Tyr Glu Glu Val Tyr Glu Thr Val Met Asn Lys Pro
210                 215                 220

Tyr Thr Arg Tyr Pro Val Tyr Glu Gly Asp Ile Asp Asn Ile Ile Gly
225                 230                 235                 240

Val Phe His Ser Lys Tyr Leu Leu Ala Trp Ser Asn Lys Lys Glu Asn
                245                 250                 255

Gln Ile Thr Asn Tyr Ser Ala Lys Pro Leu Phe Val Asn Glu His Asn
                260                 265                 270

Lys Ala Glu Trp Val Leu Arg Lys Met Thr Ile Ser Arg Lys His Leu
            275                 280                 285

Ala Ile Val Leu Asp Glu Phe Gly Gly Thr Glu Ala Ile Val Ser His
290                 295                 300

Glu Asp Leu Ile Glu Glu Leu Leu Gly Met Glu Ile Glu Asp Glu Met
305                 310                 315                 320

Asp Lys Lys Glu Lys Glu Lys Leu Ser Gln Gln Gln Ile Gln Phe Gln
                325                 330                 335

Gln Arg Lys Asn Arg Asn Val Ser Ile
            340                 345

<210> SEQ ID NO 20
<211> LENGTH: 133
<212> TYPE: PRT
<213> ORGANISM: Staphylococcus aureus

<400> SEQUENCE: 20

Met Asn Lys Gln Gln Lys Glu Phe Lys Ser Phe Tyr Ser Ile Arg Lys
 1               5                  10                  15

Ser Ser Leu Gly Val Ala Ser Val Ala Ile Ser Thr Leu Leu Leu Leu
                20                  25                  30

Met Ser Asn Gly Glu Ala Gln Ala Ala Ala Glu Glu Thr Gly Gly Thr
            35                  40                  45

Asn Thr Glu Ala Gln Pro Lys Thr Glu Ala Val Ala Ser Pro Thr Thr
 50                  55                  60

Thr Ser Glu Lys Ala Pro Glu Thr Lys Pro Val Ala Asn Ala Val Ser
 65                  70                  75                  80
```

```
Val Ser Asn Lys Glu Val Glu Ala Pro Thr Ser Glu Thr Lys Glu Ala
            85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
            115                 120                 125

Leu Ile Arg Ser Asp
            130

<210> SEQ ID NO 21
<211> LENGTH: 205
<212> TYPE: PRT
<213> ORGANISM: Staphylococcus aureus

<400> SEQUENCE: 21

Asp His Gly Ile Val Phe Asn Ala Ser Leu Pro Leu Tyr Lys Asp Ala
 1               5                  10                  15

Ile His Gln Lys Gly Ser Met Arg Ser Asn Asp Asn Gly Asp Asp Met
            20                  25                  30

Ser Met Met Val Gly Thr Val Leu Ser Gly Phe Glu Tyr Arg Ala Gln
        35                  40                  45

Lys Glu Lys Tyr Asp Asn Leu Tyr Lys Phe Phe Lys Glu Asn Glu Lys
    50                  55                  60

Lys Tyr Gln Tyr Thr Gly Phe Thr Lys Glu Ala Ile Asn Lys Thr Gln
65                  70                  75                  80

Asn Val Gly Tyr Lys Asn Glu Tyr Phe Tyr Ile Thr Tyr Ser Ser Arg
                85                  90                  95

Ser Leu Lys Glu Tyr Arg Lys Tyr Tyr Glu Pro Leu Ile Arg Lys Asn
            100                 105                 110

Asp Lys Glu Phe Lys Glu Gly Met Glu Arg Ala Arg Lys Glu Val Asn
            115                 120                 125

Tyr Ala Ala Asn Thr Asp Ala Val Ala Thr Leu Phe Ser Thr Lys Lys
            130                 135                 140

Asn Phe Thr Lys Asp Asn Thr Val Asp Val Ile Glu Leu Ser Asp
145                 150                 155                 160

Lys Leu Tyr Asn Leu Lys Asn Lys Pro Asp Lys Ser Thr Ile Thr Ile
                165                 170                 175

Gln Ile Gly Lys Pro Thr Ile Asn Thr Lys Lys Ala Phe Tyr Asp Asp
            180                 185                 190

Asn Arg Pro Ile Glu Tyr Gly Val His Ser Lys Asp Glu
            195                 200                 205

<210> SEQ ID NO 22
<211> LENGTH: 510
<212> TYPE: PRT
<213> ORGANISM: Staphylococcus aureus

<400> SEQUENCE: 22

Asp His Tyr Val Ile Gln Tyr Phe Ser Gly Leu Ile Gly Gly Arg Gly
 1               5                  10                  15

Arg Arg Ala Asn Leu Tyr Gly Leu Phe Asn Lys Ala Ile Glu Phe Glu
            20                  25                  30

Asn Ser Ser Phe Arg Gly Leu Tyr Gln Phe Ile Arg Phe Ile Asp Glu
        35                  40                  45

Leu Ile Glu Arg Gly Lys Asp Phe Gly Glu Glu Asn Val Val Gly Pro
    50                  55                  60
```

```
Asn Asp Asn Val Val Arg Met Met Thr Ile His Ser Ser Lys Gly Leu
 65                  70                  75                  80

Glu Phe Pro Phe Val Ile Tyr Ser Gly Leu Ser Lys Asp Phe Asn Lys
                 85                  90                  95

Arg Asp Leu Lys Gln Pro Val Ile Leu Asn Gln Gln Phe Gly Leu Gly
            100                 105                 110

Met Asp Tyr Phe Asp Val Asp Lys Glu Met Ala Phe Pro Ser Leu Ala
            115                 120                 125

Ser Val Ala Tyr Arg Ala Val Ala Glu Lys Glu Leu Val Ser Glu Glu
        130                 135                 140

Met Arg Leu Val Tyr Val Ala Leu Thr Arg Ala Lys Glu Gln Leu Tyr
145                 150                 155                 160

Leu Ile Gly Arg Val Lys Asn Asp Lys Ser Leu Leu Glu Leu Glu Gln
                165                 170                 175

Leu Ser Ile Ser Gly Glu His Ile Ala Val Asn Glu Arg Leu Thr Ser
            180                 185                 190

Pro Asn Pro Phe His Leu Ile Tyr Ser Ile Leu Ser Lys His Gln Ser
        195                 200                 205

Ala Ser Ile Pro Asp Asp Leu Lys Phe Glu Lys Asp Ile Ala Gln Ile
210                 215                 220

Glu Asp Ser Ser Arg Pro Asn Val Asn Ile Ser Ile Val Tyr Phe Glu
225                 230                 235                 240

Asp Val Ser Thr Glu Thr Ile Leu Asp Asn Asp Glu Tyr Arg Ser Val
                245                 250                 255

Asn Gln Leu Glu Thr Met Gln Asn Gly Asn Glu Asp Val Lys Ala Gln
            260                 265                 270

Ile Lys His Gln Leu Asp Tyr Arg Tyr Pro Tyr Val Asn Asp Thr Lys
        275                 280                 285

Lys Pro Ser Lys Gln Ser Val Ser Glu Leu Lys Arg Gln Tyr Glu Thr
290                 295                 300

Glu Glu Ser Gly Thr Ser Tyr Glu Arg Val Arg Gln Tyr Arg Ile Gly
305                 310                 315                 320

Phe Ser Thr Tyr Glu Arg Pro Lys Phe Leu Ser Glu Gln Gly Lys Arg
                325                 330                 335

Lys Ala Asn Glu Ile Gly Thr Leu Met His Thr Val Met Gln His Leu
            340                 345                 350

Pro Phe Lys Lys Glu Arg Ile Ser Glu Val Glu Leu His Gln Tyr Ile
        355                 360                 365

Asp Gly Leu Ile Asp Lys His Ile Ile Glu Ala Asp Ala Lys Lys Asp
370                 375                 380

Ile Arg Met Asp Glu Ile Met Thr Phe Ile Asn Ser Glu Leu Tyr Ser
385                 390                 395                 400

Ile Ile Ala Glu Ala Glu Gln Val Tyr Arg Glu Leu Pro Phe Val Val
                405                 410                 415

Asn Gln Ala Leu Val Asp Gln Leu Pro Gln Gly Asp Glu Asp Val Ser
            420                 425                 430

Ile Ile Gln Gly Met Ile Asp Leu Ile Phe Val Lys Asp Gly Val His
        435                 440                 445

Tyr Phe Val Asp Tyr Lys Thr Asp Ala Phe Asn Arg Arg Gly Met
450                 455                 460

Thr Asp Glu Glu Ile Gly Thr Gln Leu Lys Asn Lys Tyr Lys Ile Gln
465                 470                 475                 480
```

```
Met Lys Tyr Tyr Gln Asn Thr Leu Gln Thr Ile Leu Asn Lys Glu Val
            485                 490                 495

Lys Gly Tyr Leu Tyr Phe Phe Lys Phe Gly Thr Leu Gln Leu
            500                 505                 510

<210> SEQ ID NO 23
<211> LENGTH: 124
<212> TYPE: PRT
<213> ORGANISM: Staphylococcus aureus

<400> SEQUENCE: 23

Met Lys Phe Leu Ser Phe Lys Tyr Asn Asp Lys Thr Ser Tyr Gly Val
1               5                   10                  15

Lys Val Lys Arg Glu Asp Ala Val Trp Asp Leu Thr Gln Val Phe Ala
            20                  25                  30

Asp Phe Ala Glu Gly Asp Phe His Pro Lys Thr Leu Leu Ala Gly Leu
        35                  40                  45

Gln Gln Asn His Thr Leu Asp Phe Gln Glu Gln Val Arg Lys Ala Val
    50                  55                  60

Val Ala Ala Glu Asp Ser Gly Lys Ala Glu Asp Tyr Lys Ile Ser Phe
65                  70                  75                  80

Asn Asp Ile Glu Phe Leu Pro Pro Val Thr Pro Asn Asn Val Ile
                85                  90                  95

Ala Phe Gly Arg Asn Tyr Lys Asp His Ala Asn Glu Leu Asn His Glu
            100                 105                 110

Val Glu Lys Leu Tyr Val Phe Thr Lys Ala Ala Ser
            115                 120

<210> SEQ ID NO 24
<211> LENGTH: 180
<212> TYPE: PRT
<213> ORGANISM: Staphylococcus aureus

<400> SEQUENCE: 24

Ser Gly Thr Gly Phe Ile Val Gly Lys Asn Thr Ile Val Thr Asn Lys
1               5                   10                  15

His Val Val Ala Gly Met Glu Ile Gly Ala His Ile Ala His Pro
            20                  25                  30

Asn Gly Glu Tyr Asn Asn Gly Gly Phe Tyr Lys Val Lys Lys Ile Val
        35                  40                  45

Arg Tyr Ser Gly Gln Glu Asp Ile Ala Ile Leu His Val Glu Asp Lys
    50                  55                  60

Ala Val His Pro Lys Asn Arg Asn Phe Lys Asp Tyr Thr Gly Ile Leu
65                  70                  75                  80

Lys Ile Ala Ser Glu Ala Lys Glu Asn Glu Arg Ile Ser Ile Val Gly
                85                  90                  95

Tyr Pro Glu Pro Tyr Ile Asn Lys Phe Gln Met Tyr Glu Ser Thr Gly
            100                 105                 110

Lys Val Leu Ser Val Lys Gly Asn Met Ile Ile Thr Asp Ala Phe Val
            115                 120                 125

Glu Pro Gly Asn Ser Gly Ser Ala Val Phe Asn Ser Lys Tyr Glu Val
        130                 135                 140

Val Gly Val His Phe Gly Gly Asn Gly Pro Gly Asn Lys Ser Thr Lys
145                 150                 155                 160
```

-continued

```
Gly Tyr Gly Val Tyr Phe Ser Pro Glu Ile Lys Lys Phe Ile Ala Asp
                165                 170                 175

Asn Thr Asp Lys
            180

<210> SEQ ID NO 25
<211> LENGTH: 239
<212> TYPE: PRT
<213> ORGANISM: Staphylococcus aureus

<400> SEQUENCE: 25

Met Asn Lys Asn Ile Ile Lys Ser Ile Ala Ala Leu Thr Ile Leu
  1               5                  10                  15

Thr Ser Ile Thr Gly Val Gly Thr Thr Met Val Glu Gly Ile Gln Gln
                 20                  25                  30

Thr Ala Lys Ala Glu Asn Thr Val Lys Gln Ile Thr Asn Thr Asn Val
             35                  40                  45

Ala Pro Tyr Ser Gly Val Thr Trp Met Gly Ala Gly Thr Gly Phe Val
         50                  55                  60

Val Gly Asn His Thr Ile Ile Thr Asn Lys His Val Thr Tyr His Met
 65                  70                  75                  80

Lys Val Gly Asp Glu Ile Lys Ala His Pro Asn Gly Phe Tyr Asn Asn
                 85                  90                  95

Gly Gly Gly Leu Tyr Lys Val Thr Lys Ile Val Asp Tyr Pro Gly Lys
            100                 105                 110

Glu Asp Ile Ala Val Val Gln Val Glu Glu Lys Ser Thr Gln Pro Lys
        115                 120                 125

Gly Arg Lys Phe Lys Asp Phe Thr Ser Lys Phe Asn Ile Ala Ser Glu
    130                 135                 140

Ala Lys Glu Asn Glu Pro Ile Ser Val Ile Gly Tyr Pro Asn Pro Asn
145                 150                 155                 160

Gly Asn Lys Leu Gln Met Tyr Glu Ser Thr Gly Lys Val Leu Ser Val
                165                 170                 175

Asn Gly Asn Ile Val Ser Ser Asp Ala Ile Ile Gln Pro Gly Ser Ser
            180                 185                 190

Gly Ser Pro Ile Leu Asn Ser Lys His Glu Ala Ile Gly Val Ile Tyr
        195                 200                 205

Ala Gly Asn Lys Pro Ser Gly Glu Ser Thr Arg Gly Phe Ala Val Tyr
    210                 215                 220

Phe Ser Pro Glu Ile Lys Lys Phe Ile Ala Asp Asn Leu Asp Lys
225                 230                 235

<210> SEQ ID NO 26
<211> LENGTH: 470
<212> TYPE: PRT
<213> ORGANISM: Staphylococcus aureus

<400> SEQUENCE: 26

Met Gly Cys Thr Val Lys Met Asn Lys Ile Asn Asp Arg Asp Leu Thr
  1               5                  10                  15

Glu Leu Ser Ser Tyr Trp Val Tyr Gln Asn Ile Asp Ile Lys Lys Glu
                 20                  25                  30

Phe Lys Val Asn Gly Lys Arg Phe Lys Gln Val Asp Ser Tyr Asn Asp
             35                  40                  45

Asp Lys Asn Ser Asn Leu Asn Gly Ala Ala Asp Ile Lys Ile Tyr Glu
         50                  55                  60
```

-continued

```
Leu Leu Asp Asp Lys Ser Lys Pro Thr Gly Gln Gln Thr Ile Ile Tyr
 65                  70                  75                  80

Gln Gly Thr Ser Asn Glu Ala Ile Asn Pro Asn Asn Pro Leu Lys Ser
                 85                  90                  95

Ser Gly Phe Gly Asp Asp Trp Leu Gln Asn Ala Lys Leu Met Asn Asn
            100                 105                 110

Asp Asn Glu Ser Thr Asp Tyr Leu Lys Gln Thr Asp Gln Leu Ser Asn
        115                 120                 125

Gln Tyr Lys Ile Lys Leu Glu Asp Ala Asp Arg Leu Ser Asn Ser Asp
    130                 135                 140

Phe Leu Lys Lys Tyr Arg Met Glu Ser Ser Asn Phe Lys Asn Lys Thr
145                 150                 155                 160

Ile Val Ala Asp Gly Gly Asn Ser Glu Gly Ala Gly Ala Lys Tyr
                165                 170                 175

Gln Gly Ala Lys His Pro Asn Glu Lys Val Val Ala Thr Asp Ser Ala
            180                 185                 190

Met Ile Pro Tyr Ala Ala Trp Gln Lys Phe Ala Arg Pro Arg Phe Asp
        195                 200                 205

Asn Met Ile Ser Phe Asn Ser Thr Asn Asp Leu Leu Thr Trp Leu Gln
    210                 215                 220

Asp Pro Phe Ile Lys Asp Met Pro Gly Lys Arg Val Asn Ile Asn Asp
225                 230                 235                 240

Gly Val Pro Arg Leu Asp Thr Leu Ile Asp Ser His Val Gly Tyr Lys
                245                 250                 255

Arg Lys Leu Asn Arg Lys Asp Asn Thr Tyr Asp Thr Val Pro Leu Ile
            260                 265                 270

Lys Ile Lys Ser Val Lys Asp Thr Glu Ile Lys Asn Gly Lys Lys Val
        275                 280                 285

Lys Lys Thr Ile Asn Ile Thr Leu Asp Met Asp Gly Arg Ile Pro Ile
    290                 295                 300

Asn Val Trp Thr Gly Asp Ser Ile Ala Arg Ser Gly Arg Gly Thr Leu
305                 310                 315                 320

Ile Lys Leu Asn Leu Glu Asn Leu Asp Ala Leu Ser Lys Leu Ile Thr
                325                 330                 335

Gly Glu Thr Ser Gly Met Leu Ala Glu Cys Val Ile Phe Leu Asn Glu
            340                 345                 350

Ser Phe Asn Ile Ser Glu Asn Glu Asn Lys Asn Phe Ala Asp Arg Lys
        355                 360                 365

Lys Gln Leu Ser Glu Gly Phe Lys Asp Lys Ile Asn Leu Phe Gln Leu
    370                 375                 380

Glu Glu Met Glu Arg Thr Leu Ile Ser Lys Ile Asn Ser Leu Glu Glu
385                 390                 395                 400

Val Ala Asp Glu Thr Ile Glu Ser Ile Ser Ala Val Lys His Leu Leu
                405                 410                 415

Pro Asp Phe Ala Leu Asp Ala Leu Lys Glu Arg Ile Asn Glu Leu Phe
            420                 425                 430

Lys Gly Ile Lys Ser Phe Ile Glu Lys Val Tyr Asp Ser Ile Asp Asn
        435                 440                 445

Glu Ile Leu Glu Ile Phe Lys Asn Ile Asp His Asp Phe Arg Asp Gly
    450                 455                 460

Val Ser Glu Glu Met Met
465                 470
```

<210> SEQ ID NO 27
<211> LENGTH: 306
<212> TYPE: PRT
<213> ORGANISM: Staphylococcus aureus

<400> SEQUENCE: 27

Met Lys Lys Asp Gly Thr Gln Gln Phe Tyr His Tyr Ala Ser Ser
1               5                   10                  15

Val Lys Pro Ala Arg Val Ile Phe Thr Asp Ser Lys Pro Glu Ile Glu
            20                  25                  30

Leu Gly Leu Gln Ser Gly Gln Phe Trp Arg Lys Phe Glu Val Tyr Glu
        35                  40                  45

Gly Asp Lys Lys Leu Pro Ile Lys Leu Val Ser Tyr Asp Thr Val Lys
    50                  55                  60

Asp Tyr Ala Tyr Ile Arg Phe Ser Val Ser Asn Gly Thr Lys Ala Val
65                  70                  75                  80

Lys Ile Val Ser Ser Thr His Phe Asn Asn Lys Glu Glu Lys Tyr Asp
                85                  90                  95

Tyr Thr Leu Met Glu Phe Ala Gln Pro Ile Tyr Asn Ser Ala Asp Lys
            100                 105                 110

Phe Lys Thr Glu Glu Asp Tyr Lys Ala Glu Lys Leu Leu Ala Pro Tyr
        115                 120                 125

Lys Lys Ala Lys Thr Leu Glu Arg Gln Val Tyr Glu Leu Asn Lys Ile
    130                 135                 140

Gln Asp Lys Leu Pro Glu Lys Leu Lys Ala Glu Tyr Lys Lys Lys Leu
145                 150                 155                 160

Glu Asp Thr Lys Lys Ala Leu Asp Glu Gln Val Lys Ser Ala Ile Thr
                165                 170                 175

Glu Phe Gln Asn Val Gln Pro Thr Asn Glu Lys Met Thr Asp Leu Gln
            180                 185                 190

Asp Thr Lys Tyr Val Val Tyr Glu Ser Val Glu Asn Asn Glu Ser Met
        195                 200                 205

Met Asp Thr Phe Val Lys His Pro Ile Lys Thr Gly Met Leu Asn Gly
    210                 215                 220

Lys Lys Tyr Met Val Met Glu Thr Thr Asn Asp Asp Tyr Trp Lys Asp
225                 230                 235                 240

Phe Met Val Glu Gly Gln Arg Val Arg Thr Ile Ser Lys Asp Ala Lys
                245                 250                 255

Asn Asn Thr Arg Thr Ile Ile Phe Pro Tyr Val Glu Gly Lys Thr Leu
            260                 265                 270

Tyr Asp Ala Ile Val Lys Val His Val Lys Thr Ile Asp Tyr Asp Gly
        275                 280                 285

Gln Tyr His Val Arg Ile Val Asp Lys Glu Ala Phe Thr Lys Ala His
    290                 295                 300

Thr Asp
305

<210> SEQ ID NO 28
<211> LENGTH: 2659
<212> TYPE: PRT
<213> ORGANISM: Staphylococcus aureus

<400> SEQUENCE: 28

```
Asp Gln Thr Thr Ile Ile Asn Ser Leu Thr Phe Thr Glu Thr Val Pro
  1               5                  10                  15

Asn Arg Ser Tyr Ala Arg Ala Ser Ala Asn Glu Ile Thr Ser Lys Thr
             20                  25                  30

Val Ser Asn Val Ser Arg Thr Gly Asn Asn Ala Asn Val Thr Val Thr
         35                  40                  45

Val Thr Tyr Gln Asp Gly Thr Thr Ser Thr Val Pro Val Lys
     50                  55                  60

His Val Ile Pro Glu Ile Val Ala His Ser His Tyr Thr Val Gln Gly
 65                  70                  75                  80

Gln Asp Phe Pro Ala Gly Asn Gly Ser Ser Ala Ser Asp Tyr Phe Lys
                 85                  90                  95

Leu Ser Asn Gly Ser Asp Ile Ala Asp Ala Thr Ile Thr Trp Val Ser
            100                 105                 110

Gly Gln Ala Pro Asn Lys Asp Asn Thr Arg Ile Gly Glu Asp Ile Thr
        115                 120                 125

Val Thr Ala His Ile Leu Ile Asp Gly Glu Thr Thr Pro Ile Thr Lys
    130                 135                 140

Thr Ala Thr Tyr Lys Val Val Arg Thr Val Pro Lys His Val Phe Glu
145                 150                 155                 160

Thr Ala Arg Gly Val Leu Tyr Pro Gly Val Ser Asp Met Tyr Asp Ala
                165                 170                 175

Lys Gln Tyr Val Lys Pro Val Asn Asn Ser Trp Ser Thr Asn Ala Gln
            180                 185                 190

His Met Asn Phe Gln Phe Val Gly Thr Tyr Gly Pro Asn Lys Asp Val
        195                 200                 205

Val Gly Ile Ser Thr Arg Leu Ile Arg Val Thr Tyr Asp Asn Arg Gln
    210                 215                 220

Thr Glu Asp Leu Thr Ile Leu Ser Lys Val Lys Pro Asp Pro Pro Arg
225                 230                 235                 240

Ile Asp Ala Asn Ser Val Thr Tyr Lys Ala Gly Leu Thr Asn Gln Glu
                245                 250                 255

Ile Lys Val Asn Asn Val Leu Asn Asn Ser Ser Val Lys Leu Phe Lys
            260                 265                 270

Ala Asp Asn Thr Pro Leu Asn Val Thr Asn Ile Thr His Gly Ser Gly
        275                 280                 285

Phe Ser Ser Val Val Thr Val Ser Asp Ala Leu Pro Asn Gly Gly Ile
    290                 295                 300

Lys Ala Lys Ser Ser Ile Ser Met Asn Asn Val Thr Tyr Thr Thr Gln
305                 310                 315                 320

Asp Glu His Gly Gln Val Val Thr Val Thr Arg Asn Glu Ser Val Asp
                325                 330                 335

Ser Asn Asp Ser Ala Thr Val Thr Val Thr Pro Gln Leu Gln Ala Thr
            340                 345                 350

Thr Glu Gly Ala Val Phe Ile Lys Gly Gly Asp Gly Phe Asp Phe Gly
        355                 360                 365

His Val Glu Arg Phe Ile Gln Asn Pro Pro His Gly Ala Thr Val Ala
    370                 375                 380

Trp His Asp Ser Pro Asp Thr Trp Lys Asn Thr Val Gly Asn Thr His
385                 390                 395                 400

Lys Thr Ala Val Val Thr Leu Pro Asn Gly Gln Gly Thr Arg Asn Val
                405                 410                 415
```

-continued

```
Glu Val Pro Val Lys Val Tyr Pro Val Ala Asn Ala Lys Ala Pro Ser
            420                 425                 430

Arg Asp Val Lys Gly Gln Asn Leu Thr Asn Gly Thr Asp Ala Met Asn
            435                 440                 445

Tyr Ile Thr Phe Asp Pro Asn Thr Asn Thr Asn Gly Ile Thr Ala Ala
            450                 455                 460

Trp Ala Asn Arg Gln Gln Pro Asn Asn Gln Gln Ala Gly Val Gln His
465                 470                 475                 480

Leu Asn Val Asp Val Thr Tyr Pro Gly Ile Ser Ala Ala Lys Arg Val
                485                 490                 495

Pro Val Thr Val Asn Val Tyr Gln Phe Glu Phe Pro Gln Thr Thr Tyr
            500                 505                 510

Thr Thr Thr Val Gly Gly Thr Leu Ala Ser Gly Thr Gln Ala Ser Gly
            515                 520                 525

Tyr Ala His Met Gln Asn Ala Thr Gly Leu Pro Thr Asp Gly Phe Thr
            530                 535                 540

Tyr Lys Trp Asn Arg Asp Thr Thr Gly Thr Asn Asp Ala Asn Trp Ser
545                 550                 555                 560

Ala Met Asn Lys Pro Asn Val Ala Lys Val Asn Ala Lys Tyr Asp
                565                 570                 575

Val Ile Tyr Asn Gly His Thr Phe Ala Thr Ser Leu Pro Ala Lys Phe
            580                 585                 590

Val Val Lys Asp Val Gln Pro Ala Lys Pro Thr Val Thr Glu Thr Ala
            595                 600                 605

Ala Gly Ala Ile Thr Ile Ala Pro Gly Ala Asn Gln Thr Val Asn Thr
            610                 615                 620

His Ala Gly Asn Val Thr Thr Tyr Ala Asp Lys Leu Val Ile Lys Arg
625                 630                 635                 640

Asn Gly Asn Val Val Thr Thr Phe Thr Arg Arg Asn Asn Thr Ser Pro
                645                 650                 655

Trp Val Lys Glu Ala Ser Ala Ala Thr Val Ala Gly Ile Ala Gly Thr
            660                 665                 670

Asn Asn Gly Ile Thr Val Ala Ala Gly Thr Phe Asn Pro Ala Asp Thr
            675                 680                 685

Ile Gln Val Val Ala Thr Gln Gly Ser Gly Glu Thr Val Ser Asp Glu
            690                 695                 700

Gln Arg Ser Asp Asp Phe Thr Val Ala Pro Gln Pro Asn Gln Ala
705                 710                 715                 720

Thr Thr Lys Ile Trp Gln Asn Gly His Ile Asp Ile Thr Pro Asn Asn
                725                 730                 735

Pro Ser Gly His Leu Ile Asn Pro Thr Gln Ala Met Asp Ile Ala Tyr
            740                 745                 750

Thr Glu Lys Val Gly Asn Gly Ala Glu His Ser Lys Thr Ile Asn Val
            755                 760                 765

Val Arg Gly Gln Asn Asn Gln Trp Thr Ile Ala Asn Lys Pro Asp Tyr
            770                 775                 780

Val Thr Leu Asp Ala Gln Thr Gly Lys Val Thr Phe Asn Ala Asn Thr
785                 790                 795                 800

Ile Lys Pro Asn Ser Ser Ile Thr Ile Thr Pro Lys Ala Gly Thr Gly
                805                 810                 815

His Ser Val Ser Ser Asn Pro Ser Thr Leu Thr Ala Pro Ala Ala His
            820                 825                 830
```

-continued

```
Thr Val Asn Thr Thr Glu Ile Val Lys Asp Tyr Gly Ser Asn Val Thr
        835                 840                 845

Ala Ala Glu Ile Asn Asn Ala Val Gln Val Ala Asn Lys Arg Thr Ala
    850                 855                 860

Thr Ile Lys Asn Gly Thr Ala Met Pro Thr Asn Leu Ala Gly Gly Ser
865                 870                 875                 880

Thr Thr Thr Ile Pro Val Thr Val Thr Tyr Asn Asp Gly Ser Thr Glu
            885                 890                 895

Glu Val Gln Glu Ser Ile Phe Thr Lys Ala Asp Lys Arg Glu Leu Ile
        900                 905                 910

Thr Ala Lys Asn His Leu Asp Asp Pro Val Ser Thr Glu Gly Lys Lys
    915                 920                 925

Pro Gly Thr Ile Thr Gln Tyr Asn Asn Ala Met His Asn Ala Gln Gln
930                 935                 940

Gln Ile Asn Thr Ala Lys Thr Glu Ala Gln Gln Val Ile Asn Asn Glu
945                 950                 955                 960

Arg Ala Thr Pro Gln Gln Val Ser Asp Ala Leu Thr Lys Val Arg Ala
            965                 970                 975

Ala Gln Thr Lys Ile Asp Gln Ala Lys Ala Leu Leu Gln Asn Lys Glu
        980                 985                 990

Asp Asn Ser Gln Leu Val Thr Ser Lys Asn Asn Leu Gln Ser Ser Val
    995                 1000                1005

Asn Gln Val Pro Ser Thr Ala Gly Met Thr Gln Gln Ser Ile Asp Asn
    1010                1015                1020

Tyr Asn Ala Lys Lys Arg Glu Ala Glu Thr Glu Ile Thr Ala Ala Gln
1025                1030                1035                1040

Arg Val Ile Asp Asn Gly Asp Ala Thr Ala Gln Gln Ile Ser Asp Glu
            1045                1050                1055

Lys His Arg Val Asp Asn Ala Leu Thr Ala Leu Asn Gln Ala Lys His
        1060                1065                1070

Asp Leu Thr Ala Asp Thr His Ala Leu Glu Gln Ala Val Gln Gln Leu
    1075                1080                1085

Asn Arg Thr Gly Thr Thr Thr Gly Lys Lys Pro Ala Ser Ile Thr Ala
    1090                1095                1100

Tyr Asn Asn Ser Ile Arg Ala Leu Gln Ser Asp Leu Thr Ser Ala Lys
1105                1110                1115                1120

Asn Ser Ala Asn Ala Ile Ile Gln Lys Pro Ile Arg Thr Val Gln Glu
            1125                1130                1135

Val Gln Ser Ala Leu Thr Asn Val Asn Arg Val Asn Glu Arg Leu Thr
        1140                1145                1150

Gln Ala Ile Asn Gln Leu Val Pro Leu Ala Asp Asn Ser Ala Leu Lys
    1155                1160                1165

Thr Ala Lys Thr Lys Leu Asp Glu Glu Ile Asn Lys Ser Val Thr Thr
    1170                1175                1180

Asp Gly Met Thr Gln Ser Ser Ile Gln Ala Tyr Glu Asn Ala Lys Arg
1185                1190                1195                1200

Ala Gly Gln Thr Glu Ser Thr Asn Ala Gln Asn Val Ile Asn Asn Gly
            1205                1210                1215

Asp Ala Thr Asp Gln Gln Ile Ala Ala Glu Lys Thr Lys Val Glu Glu
        1220                1225                1230

Lys Tyr Asn Ser Leu Lys Gln Ala Ile Ala Gly Leu Thr Pro Asp Leu
    1235                1240                1245
```

-continued

```
Ala Pro Leu Gln Thr Ala Lys Thr Gln Leu Gln Asn Asp Ile Asp Gln
    1250                1255                1260

Pro Thr Ser Thr Thr Gly Met Thr Ser Ala Ser Ile Ala Ala Phe Asn
1265                1270                1275                1280

Glu Lys Leu Ser Ala Ala Arg Thr Lys Ile Gln Glu Ile Asp Arg Val
            1285                1290                1295

Leu Ala Ser His Pro Asp Val Ala Thr Ile Arg Gln Asn Val Thr Ala
        1300                1305                1310

Ala Asn Ala Ala Lys Ser Ala Leu Asp Gln Ala Arg Asn Gly Leu Thr
    1315                1320                1325

Val Asp Lys Ala Pro Leu Glu Asn Ala Lys Asn Gln Leu Gln Tyr Ser
1330                1335                1340

Ile Asp Thr Gln Thr Ser Thr Thr Gly Met Thr Gln Asp Ser Ile Asn
1345                1350                1355                1360

Ala Tyr Asn Ala Lys Leu Thr Ala Ala Arg Asn Lys Ile Gln Gln Ile
            1365                1370                1375

Asn Gln Val Leu Ala Gly Ser Pro Thr Val Glu Gln Ile Asn Thr Asn
        1380                1385                1390

Thr Ser Thr Ala Asn Gln Ala Lys Ser Asp Leu Asp His Ala Arg Gln
    1395                1400                1405

Ala Leu Thr Pro Asp Lys Ala Pro Leu Gln Thr Ala Lys Thr Gln Leu
    1410                1415                1420

Glu Gln Ser Ile Asn Gln Pro Thr Asp Thr Thr Gly Met Thr Thr Ala
1425                1430                1435                1440

Ser Leu Asn Ala Tyr Asn Gln Lys Leu Gln Ala Ala Arg Gln Lys Leu
            1445                1450                1455

Thr Glu Ile Asn Gln Val Leu Asn Gly Asn Pro Thr Val Gln Asn Ile
        1460                1465                1470

Asn Asp Lys Val Thr Glu Ala Asn Gln Ala Lys Asp Gln Leu Asn Thr
    1475                1480                1485

Ala Arg Gln Gly Leu Thr Leu Asp Arg Gln Pro Ala Leu Thr Thr Leu
    1490                1495                1500

His Gly Ala Ser Asn Leu Asn Gln Ala Gln Gln Asn Asn Phe Thr Gln
1505                1510                1515                1520

Gln Ile Asn Ala Ala Gln Asn His Ala Ala Leu Glu Thr Ile Lys Ser
            1525                1530                1535

Asn Ile Thr Ala Leu Asn Thr Ala Met Thr Lys Leu Lys Asp Ser Val
        1540                1545                1550

Ala Asp Asn Asn Thr Ile Lys Ser Asp Gln Asn Tyr Thr Asp Ala Thr
    1555                1560                1565

Pro Ala Asn Lys Gln Ala Tyr Asp Asn Ala Val Asn Ala Ala Lys Gly
    1570                1575                1580

Val Ile Gly Glu Thr Thr Asn Pro Thr Met Asp Val Asn Thr Val Asn
1585                1590                1595                1600

Gln Lys Ala Ala Ser Val Lys Ser Thr Lys Asp Ala Leu Asp Gly Gln
            1605                1610                1615

Gln Asn Leu Gln Arg Ala Lys Thr Glu Ala Thr Asn Ala Ile Thr His
        1620                1625                1630

Ala Ser Asp Leu Asn Gln Ala Gln Lys Asn Ala Leu Thr Gln Gln Val
    1635                1640                1645

Asn Ser Ala Gln Asn Val Gln Ala Val Asn Asp Ile Lys Gln Thr Thr
    1650                1655                1660
```

```
Gln Ser Leu Asn Thr Ala Met Thr Gly Leu Lys Arg Gly Val Ala Asn
1665                1670                1675                1680

His Asn Gln Val Val Gln Ser Asp Asn Tyr Val Ala Asp Thr Asn
            1685                1690                1695

Lys Lys Asn Asp Tyr Asn Asn Ala Tyr Asn His Ala Asn Asp Ile Ile
            1700                1705                1710

Asn Gly Asn Ala Gln His Pro Val Ile Thr Pro Ser Asp Val Asn Asn
        1715                1720                1725

Ala Leu Ser Asn Val Thr Ser Lys Glu His Ala Leu Asn Gly Glu Ala
    1730                1735                1740

Lys Leu Asn Ala Ala Lys Gln Glu Ala Asn Thr Ala Leu Gly His Leu
1745                1750                1755                1760

Asn Asn Leu Asn Asn Ala Gln Arg Gln Asn Leu Gln Ser Gln Ile Asn
            1765                1770                1775

Gly Ala His Gln Ile Asp Ala Val Asn Thr Ile Lys Gln Asn Ala Thr
            1780                1785                1790

Asn Leu Asn Ser Ala Met Gly Asn Leu Arg Gln Ala Val Ala Asp Lys
        1795                1800                1805

Asp Gln Val Lys Arg Thr Glu Asp Tyr Ala Asp Ala Asp Thr Ala Lys
    1810                1815                1820

Gln Asn Ala Tyr Asn Ser Ala Val Ser Ser Ala Glu Thr Ile Ile Asn
1825                1830                1835                1840

Gln Thr Thr Asn Pro Thr Met Ser Val Asp Asp Val Asn Arg Ala Thr
            1845                1850                1855

Ser Ala Val Thr Ser Asn Lys Asn Ala Leu Asn Gly Tyr Glu Lys Leu
        1860                1865                1870

Ala Gln Ser Lys Thr Asp Ala Ala Arg Ala Ile Asp Ala Leu Pro His
        1875                1880                1885

Leu Asn Asn Ala Gln Lys Ala Asp Val Lys Ser Lys Ile Asn Ala Ala
        1890                1895                1900

Ser Asn Ile Ala Gly Val Asn Thr Val Lys Gln Gln Gly Thr Asp Leu
1905                1910                1915                1920

Asn Thr Ala Met Gly Asn Leu Gln Gly Ala Ile Asn Asp Glu Gln Thr
            1925                1930                1935

Thr Leu Asn Ser Gln Asn Tyr Gln Asp Ala Thr Pro Ser Lys Lys Thr
        1940                1945                1950

Ala Tyr Thr Asn Ala Val Gln Ala Ala Lys Asp Ile Leu Asn Lys Ser
        1955                1960                1965

Asn Gly Gln Asn Lys Thr Lys Asp Gln Val Thr Glu Ala Met Asn Gln
    1970                1975                1980

Val Asn Ser Ala Lys Asn Asn Leu Asp Gly Thr Arg Leu Leu Asp Gln
1985                1990                1995                2000

Ala Lys Gln Thr Ala Lys Gln Gln Leu Asn Asn Met Thr His Leu Thr
            2005                2010                2015

Thr Ala Gln Lys Thr Asn Leu Thr Asn Gln Ile Asn Ser Gly Thr Thr
        2020                2025                2030

Val Ala Gly Val Gln Thr Val Gln Ser Asn Ala Asn Thr Leu Asp Gln
    2035                2040                2045

Ala Met Asn Thr Leu Arg Gln Ser Ile Ala Asn Lys Asp Ala Thr Lys
    2050                2055                2060

Ala Ser Glu Asp Tyr Val Asp Ala Asn Asn Asp Lys Gln Thr Ala Tyr
2065                2070                2075                2080
```

-continued

Asn Asn Ala Val Ala Ala Ala Glu Thr Ile Ile Asn Ala Asn Ser Asn
            2085                2090                2095

Pro Glu Met Asn Pro Ser Thr Ile Thr Gln Lys Ala Glu Gln Val Asn
        2100                2105                2110

Ser Ser Lys Thr Ala Leu Asn Gly Asp Glu Asn Leu Ala Ala Ala Lys
        2115                2120                2125

Gln Asn Ala Lys Thr Tyr Leu Asn Thr Leu Thr Ser Ile Thr Asp Ala
        2130                2135                2140

Gln Lys Asn Asn Leu Ile Ser Gln Ile Thr Ser Ala Thr Arg Val Ser
2145                2150                2155                2160

Gly Val Asp Thr Val Lys Gln Asn Ala Gln His Leu Asp Gln Ala Met
            2165                2170                2175

Ala Ser Leu Gln Asn Gly Ile Asn Asn Glu Ser Gln Val Lys Ser Ser
            2180                2185                2190

Glu Lys Tyr Arg Asp Ala Asp Thr Asn Lys Gln Gln Glu Tyr Asp Asn
            2195                2200                2205

Ala Ile Thr Ala Ala Lys Ala Ile Leu Asn Lys Ser Thr Gly Pro Asn
            2210                2215                2220

Thr Ala Gln Asn Ala Val Glu Ala Ala Leu Gln Arg Val Asn Asn Ala
2225                2230                2235                2240

Lys Asp Ala Leu Asn Gly Asp Ala Lys Leu Ile Ala Ala Gln Asn Ala
            2245                2250                2255

Ala Lys Gln His Leu Gly Thr Leu Thr His Ile Thr Thr Ala Gln Arg
            2260                2265                2270

Asn Asp Leu Thr Asn Gln Ile Ser Gln Ala Thr Asn Leu Ala Gly Val
            2275                2280                2285

Glu Ser Val Lys Gln Asn Ala Asn Ser Leu Asp Gly Ala Met Gly Asn
            2290                2295                2300

Leu Gln Thr Ala Ile Asn Asp Lys Ser Gly Thr Leu Ala Ser Gln Asn
2305                2310                2315                2320

Phe Leu Asp Ala Asp Glu Gln Lys Arg Asn Ala Tyr Asn Gln Ala Val
            2325                2330                2335

Ser Ala Ala Glu Thr Ile Leu Asn Lys Gln Thr Gly Pro Asn Thr Ala
            2340                2345                2350

Lys Thr Ala Val Glu Gln Ala Leu Asn Asn Val Asn Asn Ala Lys His
            2355                2360                2365

Ala Leu Asn Gly Thr Gln Asn Leu Asn Asn Ala Lys Gln Ala Ala Ile
            2370                2375                2380

Thr Ala Ile Asn Gly Ala Ser Asp Leu Asn Gln Lys Gln Lys Asp Ala
2385                2390                2395                2400

Leu Lys Ala Gln Ala Asn Gly Ala Gln Arg Val Ser Asn Ala Gln Asp
            2405                2410                2415

Val Gln His Asn Ala Thr Glu Leu Asn Thr Ala Met Gly Thr Leu Lys
            2420                2425                2430

His Ala Ile Ala Asp Lys Thr Asn Thr Leu Ala Ser Ser Lys Tyr Val
            2435                2440                2445

Asn Ala Asp Ser Thr Lys Gln Asn Ala Tyr Thr Thr Lys Val Thr Asn
            2450                2455                2460

Ala Glu His Ile Ile Ser Gly Thr Pro Thr Val Thr Thr Pro Ser
2465                2470                2475                2480

Glu Val Thr Ala Ala Ala Asn Gln Val Asn Ser Ala Lys Gln Glu Leu
            2485                2490                2495

Asn Gly Asp Glu Arg Leu Arg Glu Ala Lys Gln Asn Ala Asn Thr Ala
         2500               2505               2510

Ile Asp Ala Leu Thr Gln Leu Asn Thr Pro Gln Lys Ala Lys Leu Lys
         2515               2520               2525

Glu Gln Val Gly Gln Ala Asn Arg Leu Glu Asp Val Gln Thr Val Gln
         2530               2535               2540

Thr Asn Gly Gln Ala Leu Asn Asn Ala Met Lys Gly Leu Arg Asp Ser
2545               2550               2555               2560

Ile Ala Asn Glu Thr Thr Val Lys Thr Ser Gln Asn Tyr Thr Asp Ala
         2565               2570               2575

Ser Pro Asn Asn Gln Ser Thr Tyr Asn Ser Ala Val Ser Asn Ala Lys
         2580               2585               2590

Gly Ile Ile Asn Gln Thr Asn Asn Pro Thr Met Asp Thr Ser Ala Ile
         2595               2600               2605

Thr Gln Ala Thr Thr Gln Val Asn Asn Ala Lys Asn Gly Leu Asn Gly
         2610               2615               2620

Ala Glu Asn Leu Arg Asn Ala Gln Asn Thr Ala Lys Gln Asn Leu Asn
2625               2630               2635               2640

Thr Leu Ser His Leu Thr Asn Asn Gln Lys Ser Ala Ile Ser Ser Gln
         2645               2650               2655

Ile Asp Arg

<210> SEQ ID NO 29
<211> LENGTH: 496
<212> TYPE: PRT
<213> ORGANISM: Staphylococcus aureus

<400> SEQUENCE: 29

Met Asn Met Lys Lys Lys Glu Lys His Ala Ile Arg Lys Lys Ser Ile
1               5                  10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
            85                  90                  95

Glu Thr Thr Gln Ser Ser Ser Thr Asn Ala Thr Thr Glu Glu Thr Pro
        100                 105                 110

Val Thr Gly Glu Ala Thr Thr Thr Thr Thr Asn Gln Ala Asn Thr Pro
    115                 120                 125

Ala Thr Thr Gln Ser Ser Asn Thr Asn Ala Glu Glu Leu Val Asn Gln
130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
        180                 185                 190

Ser Thr Asp Ala Ser Asn Lys Asp Val Val Asn Gln Ala Val Asn Thr
    195                 200                 205

```
Ser Ala Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
290                 295                 300

Ala Asn Gly Val Ile Asp Ser Asp Gly Asn Val Ile Tyr Thr Phe Thr
305                 310                 315                 320

Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

<210> SEQ ID NO 30
<211> LENGTH: 541
<212> TYPE: PRT
<213> ORGANISM: Staphylococcus aureus

<400> SEQUENCE: 30

Asp Gln Tyr Leu Leu Glu Arg Lys Lys Ser Gln Tyr Glu Asp Tyr Lys
1               5                   10                  15

Gln Trp Tyr Ala Asn Tyr Lys Lys Glu Asn Pro Arg Thr Asp Leu Lys
            20                  25                  30

Met Ala Asn Phe His Lys Tyr Asn Leu Glu Glu Leu Ser Met Lys Glu
        35                  40                  45

Tyr Asn Glu Leu Gln Asp Ala Leu Lys Arg Ala Leu Asp Asp Phe His
    50                  55                  60

Arg Glu Val Lys Asp Ile Lys Asp Lys Asn Ser Asp Leu Lys Thr Phe
65                  70                  75                  80

Asn Ala Ala Glu Glu Asp Lys Ala Thr Lys Glu Val Tyr Asp Leu Val
                85                  90                  95
```

```
Ser Glu Ile Asp Thr Leu Val Val Ser Tyr Tyr Gly Asp Lys Asp Tyr
            100                 105                 110

Gly Glu His Ala Lys Glu Leu Arg Ala Lys Leu Asp Leu Ile Leu Gly
            115                 120                 125

Asp Thr Asp Asn Pro His Lys Ile Thr Asn Glu Arg Ile Lys Lys Glu
            130                 135                 140

Met Ile Asp Asp Leu Asn Ser Ile Ile Asp Asp Phe Phe Met Glu Thr
145                 150                 155                 160

Lys Gln Asn Arg Pro Lys Ser Ile Thr Lys Tyr Asn Pro Thr Thr His
                165                 170                 175

Asn Tyr Lys Thr Asn Ser Asp Asn Lys Pro Asn Phe Asp Lys Leu Val
            180                 185                 190

Glu Glu Thr Lys Lys Ala Val Lys Glu Ala Asp Asp Ser Trp Lys Lys
            195                 200                 205

Lys Thr Val Lys Lys Tyr Gly Glu Thr Glu Thr Lys Ser Pro Val Val
            210                 215                 220

Lys Glu Glu Lys Lys Val Glu Glu Pro Gln Ala Pro Lys Val Asp Asn
225                 230                 235                 240

Gln Gln Glu Val Lys Thr Thr Ala Gly Lys Ala Glu Glu Thr Thr Gln
                245                 250                 255

Pro Val Ala Gln Pro Leu Val Lys Ile Pro Gln Gly Thr Ile Thr Gly
            260                 265                 270

Glu Ile Val Lys Gly Pro Glu Tyr Pro Thr Met Glu Asn Lys Thr Val
            275                 280                 285

Gln Gly Glu Ile Val Gln Gly Pro Asp Phe Leu Thr Met Glu Gln Ser
            290                 295                 300

Gly Pro Ser Leu Ser Asn Asn Tyr Thr Asn Pro Pro Leu Thr Asn Pro
305                 310                 315                 320

Ile Leu Glu Gly Leu Glu Gly Ser Ser Lys Leu Glu Ile Lys Pro
                325                 330                 335

Gln Gly Thr Glu Ser Thr Leu Lys Gly Thr Gln Gly Glu Ser Ser Asp
            340                 345                 350

Ile Glu Val Lys Pro Gln Ala Thr Glu Thr Thr Glu Ala Ser Gln Tyr
            355                 360                 365

Gly Pro Arg Pro Gln Phe Asn Lys Thr Pro Lys Tyr Val Lys Tyr Arg
            370                 375                 380

Asp Ala Gly Thr Gly Ile Arg Glu Tyr Asn Asp Gly Thr Phe Gly Tyr
385                 390                 395                 400

Glu Ala Arg Pro Arg Phe Asn Lys Pro Ser Glu Thr Asn Ala Tyr Asn
                405                 410                 415

Val Thr Thr His Ala Asn Gly Gln Val Ser Tyr Gly Ala Arg Pro Thr
            420                 425                 430

Tyr Lys Lys Pro Ser Glu Thr Asn Ala Tyr Asn Val Thr Thr His Ala
            435                 440                 445

Asn Gly Gln Val Ser Tyr Gly Ala Arg Pro Thr Gln Asn Lys Pro Ser
            450                 455                 460

Lys Thr Asn Ala Tyr Asn Val Thr Thr His Gly Asn Gly Gln Val Ser
465                 470                 475                 480

Tyr Gly Ala Arg Gln Ala Gln Asn Lys Pro Ser Lys Thr Asn Ala Tyr
                485                 490                 495

Asn Val Thr Thr His Ala Asn Gly Gln Val Ser Tyr Gly Ala Arg Pro
            500                 505                 510
```

Thr Tyr Lys Lys Pro Ser Lys Thr Asn Ala Tyr Asn Val Thr Thr His
        515                 520                 525

Ala Asp Gly Thr Ala Thr Tyr Gly Pro Arg Val Thr Lys
530                 535                 540

<210> SEQ ID NO 31
<211> LENGTH: 356
<212> TYPE: PRT
<213> ORGANISM: Staphylococcus aureus

<400> SEQUENCE: 31

Met Lys Met Arg Thr Ile Ala Lys Thr Ser Leu Ala Leu Gly Leu Leu
 1               5                  10                  15

Thr Thr Gly Ala Ile Thr Val Thr Thr Gln Ser Val Lys Ala Glu Lys
             20                  25                  30

Ile Gln Ser Thr Lys Val Asp Lys Val Pro Thr Leu Lys Ala Glu Arg
         35                  40                  45

Leu Ala Met Ile Asn Ile Thr Ala Gly Ala Asn Ser Ala Thr Thr Gln
     50                  55                  60

Ala Ala Asn Thr Arg Gln Glu Arg Thr Pro Lys Leu Glu Lys Ala Pro
 65                  70                  75                  80

Asn Thr Asn Glu Glu Lys Thr Ser Ala Ser Lys Ile Glu Lys Ile Ser
                 85                  90                  95

Gln Pro Lys Gln Glu Gln Lys Thr Leu Asn Ile Ser Ala Thr Pro
            100                 105                 110

Ala Pro Lys Gln Glu Gln Ser Gln Thr Thr Thr Glu Ser Thr Thr Pro
        115                 120                 125

Lys Thr Lys Val Thr Thr Pro Ser Thr Asn Thr Pro Gln Pro Met
    130                 135                 140

Gln Ser Thr Lys Ser Asp Thr Pro Gln Ser Pro Thr Ile Lys Gln Ala
145                 150                 155                 160

Gln Thr Asp Met Thr Pro Lys Tyr Glu Asp Leu Arg Ala Tyr Tyr Thr
                165                 170                 175

Lys Pro Ser Phe Glu Phe Glu Lys Gln Phe Gly Phe Met Leu Lys Pro
            180                 185                 190

Trp Thr Thr Val Arg Phe Met Asn Val Ile Pro Asn Arg Phe Ile Tyr
        195                 200                 205

Lys Ile Ala Leu Val Gly Lys Asp Glu Lys Tyr Lys Asp Gly Pro
    210                 215                 220

Tyr Asp Asn Ile Asp Val Phe Ile Val Leu Glu Asp Asn Lys Tyr Gln
225                 230                 235                 240

Leu Lys Lys Tyr Ser Val Gly Gly Ile Thr Lys Thr Asn Ser Lys Lys
                245                 250                 255

Val Asn His Lys Val Glu Leu Ser Ile Thr Lys Asp Asn Gln Gly
            260                 265                 270

Met Ile Ser Arg Asp Val Ser Glu Tyr Met Ile Thr Lys Glu Glu Ile
        275                 280                 285

Ser Leu Lys Glu Leu Asp Phe Lys Leu Arg Lys Gln Leu Ile Glu Lys
    290                 295                 300

His Asn Leu Tyr Gly Asn Met Gly Ser Gly Thr Ile Val Ile Lys Met
305                 310                 315                 320

Lys Asn Gly Gly Lys Tyr Thr Phe Glu Leu His Lys Lys Leu Gln Glu
                325                 330                 335

```
His Arg Met Ala Asp Val Ile Asp Gly Thr Asn Ile Asp Asn Ile Glu
            340                 345                 350
Val Asn Ile Lys
        355

<210> SEQ ID NO 32
<211> LENGTH: 313
<212> TYPE: PRT
<213> ORGANISM: Staphylococcus aureus

<400> SEQUENCE: 32

Met Glu His Thr Thr Met Lys Ile Thr Thr Ile Ala Lys Thr Ser Leu
  1               5                  10                  15

Ala Leu Gly Leu Leu Thr Thr Gly Val Ile Thr Thr Thr Thr Gln Ala
             20                  25                  30

Ala Asn Ala Thr Thr Leu Ser Ser Thr Lys Val Glu Ala Pro Gln Ser
         35                  40                  45

Thr Pro Pro Ser Thr Lys Ile Glu Ala Pro Gln Ser Lys Pro Asn Ala
     50                  55                  60

Thr Thr Pro Pro Ser Thr Lys Val Glu Ala Pro Gln Gln Thr Ala Asn
 65                  70                  75                  80

Ala Thr Thr Pro Pro Ser Thr Lys Val Thr Thr Pro Pro Ser Thr Asn
                 85                  90                  95

Thr Pro Gln Pro Met Gln Ser Thr Lys Ser Asp Thr Pro Gln Ser Pro
            100                 105                 110

Thr Thr Lys Gln Val Pro Thr Glu Ile Asn Pro Lys Phe Lys Asp Leu
            115                 120                 125

Arg Ala Tyr Tyr Thr Lys Pro Ser Leu Glu Phe Lys Asn Glu Ile Gly
    130                 135                 140

Ile Ile Leu Lys Lys Trp Thr Thr Ile Arg Phe Met Asn Val Val Pro
145                 150                 155                 160

Asp Tyr Phe Ile Tyr Lys Ile Ala Leu Val Gly Lys Asp Asp Lys Lys
                165                 170                 175

Tyr Gly Glu Gly Val His Arg Asn Val Asp Val Phe Val Val Leu Glu
            180                 185                 190

Glu Asn Asn Tyr Asn Leu Glu Lys Tyr Ser Val Gly Gly Ile Thr Lys
        195                 200                 205

Ser Asn Ser Lys Lys Val Asp His Lys Ala Gly Val Arg Ile Thr Lys
    210                 215                 220

Glu Asp Asn Lys Gly Thr Ile Ser His Asp Val Ser Glu Phe Lys Ile
225                 230                 235                 240

Thr Lys Glu Gln Ile Ser Leu Lys Glu Leu Asp Phe Lys Leu Arg Lys
                245                 250                 255

Gln Leu Ile Glu Lys Asn Asn Leu Tyr Gly Asn Val Gly Ser Gly Lys
            260                 265                 270

Ile Val Ile Lys Met Lys Asn Gly Gly Lys Tyr Thr Phe Glu Leu His
        275                 280                 285

Lys Lys Leu Gln Glu Asn Arg Met Ala Asp Val Ile Asp Gly Thr Asn
    290                 295                 300

Ile Asp Asn Ile Glu Val Asn Ile Lys
305                 310
```

STAPHYLOCOCCUS AUREUS ANTIGENIC POLYPEPTIDES AND COMPOSITIONS

This application is divisional application of U.S. patent application Ser. No. 10/311,879, filed Mar. 18, 2003, which is now abandoned, which is a national stage application of PCT/GB01/02685, filed Jun. 20, 2001, which claims the benefit of priority of Great Britain Application No. GB 0014907.0, filed Jun. 20, 2000, each of which is herein incorporated by reference in its entirety.

The invention relates to a method for the identification of antigenic polypeptides expressed by pathogenic microbes; vaccines comprising said polypeptides; recombinant methods to manufacture said polypeptides; and therapeutic antibodies directed to said polypeptides.

Microbial organisms cause a number of fatal or debilitating diseases which affect many millions of people around the world. Currently methods to control microbial organisms include the use of antimicrobial agents (antibiotics) and disinfectants. These have proved to be problematic since exposure to these agents places a significant selection pressure resulting in the creation of resistant microbes which can avoid the effects of the antimicrobial agent(s). For example, recently it has been discovered that microbial organisms have become resistant to triclosan, an agent added to many disinfectants used in households and industrial environments.

An arguably greater problem is the evolution of antibiotic resistant strains of a number of significant pathogenic microbes.

For example, and not by way of limitation, it is estimated that there are up to 50 million people world-wide infected with drug resistant tuberculosis (TB) (Figures from the World Health Organisation, 1998). In the past the use of antibiotics to treat TB relied on the administration of single drugs (eg ethionamide) which promoted a relatively high frequency of resistance. For this reason, combinations of drugs are now used to treat tuberculosis. However the fatality rate in cases caused by strains that are resistant to at least one drug used to treat tuberculosis still approaches 50% even when treatment is given. *Mycobacterium tuberculosis*, the causative agent of TB, is a slow growing bacteria and takes a long time to kill. Therefore, for a drug combination to be effective a person with TB must take the drug combination daily for at least six months. Accordingly, patients frequently have to take two or more pills daily and this requires a regimented dosage over a relatively long period of treatment. Many patients take the medications only intermittently and therefore do not finish the full course of therapy to completely eradicate the *M. tuberculosis* infection. Moreover, TB is strongly associated with HIV infection and therefore the establishment of TB is strongly correlated with immunosuppression.

Vaccination against TB has been available for many years. The *bacillus calmette* and guerin (BCG) vaccination has been widely used throughout the world for a long time because it is a safe and inexpensive means to vaccinate large numbers of people who potentially could contract TB. BCG is derived from live, attenuated strains of *Mycobacterium bovis*. However the impact of vaccination on the infectious forms of TB is minimal and BCG has therefore contributed little to the overall control of the disease.

A further example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this germ can cause infection. This is a particular problem in hospitals where patients may have surgical procedures and/or be taking immunosuppressive drugs. These patients are much more vulnerable to infection with *S. aureus* because of the treatment they have received. Resistant strains of *S. aureus* have arisen in recent years. Methicillin resistant strains are prevalent and many of these resistant strains are also resistant to several other antibiotics. Currently there is no effective vaccination procedure for *S. aureus*. In the US, *S. aureus* infections are the cause of 13% of the two million hospitalised infections each year. This represents 260,000 people with an infection of *S. aureus*, of which 60-80,000 die.

*S. aureus* is therefore a major human pathogen capable of causing a wide range of life threatening diseases including septicaemia, endocarditis, arthritis and toxic shock. This ability is determined by the versatility of the organism and its arsenal of components involved in virulence. Pathogenicity is multifactorial and no one component has shown to be responsible for a particular infection, see Projan, S. J. & Novick, R. P. (1997) in The Staphylococci in Human Disease (Crossley, K. B. & Archer, G. L., eds.) pp.55-81.

At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. These include collagen-, fibrinogen- and fibronectin-binding proteins. The pathogen also has the ability to evade host defences by the production of factors that reduce phagocytosis or interfere with the ability of the cells to be recognised by circulating antibodies.

Often a focus of infection develops as an abscess and the number of organisms increases. *S. aureus* has the ability to monitor its own cell density by the production of a quorum sensing peptide. Accumulation of the peptide, associated with physiological changes brought about by the beginning of starvation of the cells, elicits a switch in virulence determinant production from adhesins to components involved in invasion and tissue penetration. These include a wide range of hemolysins, proteases and other degradative enzymes.

During the process of any infection the virulence determinants made by *S. aureus* are produced in response to environmental and physiological stimuli. These stimuli will be dependent on the niche within the body and will change as the infection progresses. Little is known of the conditions in vivo and it is likely that some components are produced solely in this environment. These are therefore potential vaccine components, which could not be discovered by previous techniques.

One of the most important developments in recent medical history is the development of vaccines which provide prophylactic protection from a wide variety of pathogenic organisms. Many vaccines are produced by inactivated or attenuated pathogens which are injected into an individual. The immunised individual responds by producing both a humoral (antibody) and cellular (cytolytic T cells, CTL's) response. For example, hepatitis vaccines are made by heat inactivating the virus and treating it with a cross linking agent such as formaldehyde. An example of an attenuated pathogen useful as a vaccine is represented by polio vaccines which are produced by attenuating a live pathogen.

However the use of attenuated organisms in vaccines for certain diseases is problematic due to the lack of knowledge regarding the pathology of the condition and the nature of the attenuation. For certain viral agents this is a particular problem since viruses, in particular retroviruses, have an error prone replication cycle which results viable mutations in the genes which comprise the virus. This can result in alterations to antigenic determinants which have previously been used as vaccines. An alternative to the use of inactivated or attenuated pathogens is the identification of pathogen epitopes to which the immune system is particularly sensitive. In this regard many pathogenic toxins produced by pathogenic organisms during an infection are particularly useful in the development of vaccines which protect the individual from a particular pathogenic organism.

The development of so-called subunit vaccines (vaccines in which the immunogen is a fragment or subunit of a protein or complex expressed by a particular pathogenic organism) has been the focus of considerable medical research. The need to identify candidate molecules useful in the development of subunit vaccines is apparent not least because conventional chemotherapeutic approaches to the control of pathogenic organisms has more recently been stymied by the development of antibiotic resistance. A number of methods have been developed to identify potential antigenic polypeptides which can be used as a vaccine. One such method is disclosed herein.

It has been known for many years that tumour cells produce a number of tumour cell specific antigens, some of which are presented at the tumour cell surface. The immune system recognises these antigens as foreign thereby resulting in the production of antibodies to self antigens, so called autoantibodies or autologous antisera.

One such technique is Serological identification of antigens by recombinant Expression Cloning, abbreviated to SEREX.

Typically, the technique involves the extraction of RNA from tumour tissue followed by the selective enrichment of mRNA from the isolated total RNA. The mRNA is reverse transcribed into cDNA using viral reverse transcriptase. The cDNA thus synthesised is subcloned into an expression vector and transformed into an appropriate bacterial strain. The transformed bacteria are plated onto a suitable nutrient agar and under appropriate growth conditions the subcloned cDNA is expressed from the expression vector in the bacterial cell. The cells are lysed naturally by the use of phage based expression vectors, for example λ phage or phagemid based vectors, which through their lytic cycle cause cell lysis. The released polypeptides are transferred to a suitable membrane support (i.e. nitrocellulose, nylon) and exposed to autologous antisera from the patient from which the tumour tissue was originally isolated. The immunoscreening methodology allows the identification of genes that are over expressed or inappropriately expressed in a selected tumour tissue from a patient.

We have exploited this technique to identify antigenic polypeptides expressed by pathogenic organisms during an infection. Autologous antisera produced during the infection is used to screen an expression library created from genomic DNA to identify and clone antigens.

In its broadest aspect the invention relates to the identification of antigenic polypeptides expressed during an infection by a pathogenic microbe.

According to a first aspect of the invention there is provided a method to identify antigenic polypeptides comprising:

(i) providing a nucleic acid library encoding genes or partial gene sequences of a pathogenic organism;

(ii) transforming/transfecting said library into a host cell;

(iii) providing conditions conducive to the expression of said transformed/transfected genes or partial gene sequences;

(iv) contacting the polypeptides expressed by the genes/partial gene sequences with autologous antisera derived from an animal infected with, or has been infected with, said pathogenic organism; and (v) purifying the nucleic acid encoding the polypeptide or partial polypeptide binding to said autologous antisera.

In a preferred method of the invention said library comprises genomic DNA of a pathogenic organism.

Ideally said pathogenic organism is bacterial.

More preferably still said bacterial organism is selected from the following: *Staphylococcus aureus; Staphylococcus epidermidis; Enterococcus faecalis; Mycobacterium tuberculsis; Streptoccocus* group B; *Streptoccocus pneumoniae; Helicobacter pylori; Neisseria gonorrhea; Streptococcus* group A; *Borrelia burgdorferi; Coccidiodes immitis; Histoplasma sapsulatum; Neisseria meningitidis* type B; *Shigella flexneri; Escherichia coli; Haemophilus influenzae.*

Preferably still said pathogenic organism is of the genus *Staphylococcus* spp. Ideally organism is *Staphylococcus aureus* or *Staphylococcus epidermidis.*

In a further preferred embodiment of the invention said nucleic acid library is a lambda library, ideally a lambda expression library.

According to a second aspect of the invention there is provided a nucleic acid molecule comprising a DNA sequence selected from:

(i) the DNA sequence as represented in SEQ ID NO's 1-13;

(ii) DNA sequences which hybridise to the sequence presented in the SEQ ID No's 1-13 identified in (i) above which encode a polypeptide expressed by a pathogenic organism and (iii) DNA sequences which are degenerate as a result of the genetic code to the DNA sequences defined in (i) and (ii).

In a yet still further preferred embodiment of the invention said nucleic acid molecule is genomic DNA.

In a preferred embodiment of the invention there is provided an isolated nucleic acid molecule which anneals under stringent hybridisation conditions to the sequences presented in SEQ ID NO's 1-13.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequences of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m = 81.5^{\circ}C + 16.6\ \mathrm{Log}[Na^+] + 0.41[\%\ G+C] - 0.63(\%\ \mathrm{formamide}).$$

According to a third aspect of the invention there is provided at least one polypeptide identified by the method according to the invention.

In a preferred embodiment of the invention, said polypeptide is associated with infective pathogenicity of an organism according to any previous aspect or embodiment of the invention.

More preferably still said polypeptide is at least one, or part of SEQ ID NOs: 14-32.

According to a fourth aspect of the invention there is provided a nucleic acid molecule characterised in that said nucleic acid molecule is part of a vector adapted to facilitate recombinant expression of the polypeptide encoded by said nucleic acid molecule.

In a preferred embodiment of the invention said vector is an expression vector adapted for prokaryotic gene expression. Alternatively said expression vector is adapted for eukaryotic gene expression.

Typically said adaptation includes, by example and not by way of limitation, the provision of transcription control sequences (promoter sequences) which mediate cell specific expression. These promoter sequences may be cell specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites (eg glucose, lipids), environmental effectors (eg light, heat,).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc.(1994).

According to yet a further aspect of the invention there is provided a method for the production of the polypeptides according to any previous aspect or embodiment of the invention comprising:
(i) providing a cell transformed/transfected with a vector according to the invention;
(ii) growing said cell in conditions conducive to the manufacture of said polypeptides; and
(iii) purifying said polypeptide from said cell, or its growth environment.

In a preferred method of the invention said vector encodes, and thus said recombinant polypeptide is provided with, a secretion signal to facilitate purification of said polypeptide.

According to a fifth aspect of the invention there is provided a cell or cell-line transformed or transfected with the vector according to the invention.

In a preferred embodiment of the invention said cell is a prokaryotic cell. Alternatively said cell is a eukaryotic cell selected from: fungal, insect, amphibian; mammalian; plant.

According to a yet further aspect of the invention there is provided a vaccine comprising at least one polypeptide according to the invention.

Ideally said vaccine further comprises a carrier and/or adjuvant.

The terms adjuvant and carrier are construed in the following manner. Some polypeptide or peptide antigens contain B-cell epitopes but no T cell epitopes. Immune responses can be greatly enhanced by the inclusion of a T cell epitope in the polypeptide/peptide or by the conjugation of the polypeptide/peptide to an immunogenic carrier protein such as key hole limpet haemocyanin or tetanus toxoid which contain multiple T cell epitopes. The conjugate is taken up by antigen presenting cells, processed and presented by human leukocyte antigens (HLA's) class II molecules. This allows T cell help to be given by T cell's specific for carrier derived epitopes to the B cell which is specific for the original antigenic polypeptide/peptide. This can lead to increase in antibody production, secretion and isotype switching.

An adjuvant is a substance or procedure which augments specific immune responses to antigens by modulating the activity of immune cells. Examples of adjuvants include, by example only, agonsitic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter.

In yet a further aspect of the invention there is provided a method to immunise an animal against a pathogenic microbe comprising administering to said animal at least one polypeptide, or part thereof, according to the invention or the vaccine according to the invention.

In a preferred method of the invention said animal is human.

Preferably the vaccine, or antigenic polypeptide, can be delivered by direct injection either intravenously, intramuscularly, subcutaneously. Further still, the vaccine or antigenic polypeptide, may be taken orally.

Preferably the vaccine is against the bacterial species *Staphylococcus aureus*.

The vaccine may also be against the bacterial species *Staphylococcus epidermidis*.

It will also be apparent that vaccines or antigenic polypeptides are effective at preventing or alleviating conditions in animals other than humans, for example and not by way of limitation, family pets, livestock, horses.

According to a further aspect of the invention there is provided an antibody, or at least an effective binding part thereof, which binds at least one polypeptide according to the invention.

In a preferred embodiment of the invention said antibody is a polyclonal or monoclonal antibody wherein said antibody is specific to said polypeptide.

Alternatively, said antibody is a chimeric antibody produced by recombinant methods to contain the variable region of said antibody with an invariant or constant region of a human antibody.

In a further alternative embodiment of the invention, said antibody is humanised by recombinant methods to combine the complimentarity determining regions of said antibody with both the constant (C) regions and the framework regions from the variable (V) regions of a human antibody.

Preferably said antibody is provided with a marker including a conventional label or tag, for example a radioactive and/or fluorescent and/or epitope label or tag.

Preferably said humanised monoclonal antibody to said polypeptide is produced as a fusion polypeptide in an expression vector suitably adapted for transfection or transformation of prokaryotic or eukaryotic cells.

Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain ($\kappa$ or $\lambda$), and one pair of heavy (H) chains ($\gamma$, $\alpha$, $\mu$, $\delta$ and $\epsilon$), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, $\alpha$, $\mu$, $\sigma$, $\alpha$, and $\gamma$ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

Chimeric antibodies are recombinant antibodies in which all of the V-regions of a mouse or rat antibody are combined with human antibody C-regions. Humanised antibodies are recombinant hybrid antibodies which fuse the complimentarily determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

In another aspect of the invention there is provided a vector which is adapted for the expression of the humanised or chimeric antibodies according to the invention.

In a yet further aspect of the invention, there is provided a cell or cell line which has been transformed or transfected with the vector encoding the humanised or chimeric antibody according to the invention.

In a yet further aspect of the invention there is provided a method for the production of the humanised or chimeric antibody according to the invention comprising:
  (i) providing a cell transformed or transfected with a vector which comprises a nucleic acid molecule encoding the humanised or chimeric antibody according to the invention;
  (ii) growing said cell in conditions conducive to the manufacture of said antibody; and
  (iii) purifying said antibody from said cell, or its growth environment.

In a yet further aspect of the invention there is provided a hybridoma cell line which produces a monoclonal antibody as hereinbefore described.

In a further aspect of the invention there is provided a method of producing monoclonal antibodies according to the invention using hybridoma cell lines according to the invention.

In a further aspect of the invention there is provided a method for preparing a hybridoma cell-line producing monoclonal antibodies according to the invention comprising the steps of:
  i) immunising an immunocompetent mammal with an immunogen comprising at least one polypeptide having the amino acid sequence as represented in SEQ. ID No 14-32, or fragments thereof;
  ii) fusing lymphocytes of the immunised immunocompetent mammal with myeloma cells to form hybridoma cells;
  iii) screening monoclonal antibodies produced by the hybridoma cells of step (ii) for binding activity to the amino acid sequences of (i);
  iv) culturing the hybridoma cells to proliferate and/or to secrete said monoclonal antibody; and
  v) recovering the monoclonal antibody from the culture supernatant.

Preferably, the said immunocompetent mammal is a mouse. Alternatively, said immunocompetent mammal is a rat.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a further aspect of the invention there is provided the use of the antibodies for manufacture of a medicament for the treatment of *Staphylococcus aureus*-associated septicaemia, food-poisoning or skin disorders.

In another aspect of the invention there is provided the use of the antibodies according to the invention for the manufacture of a medicament for the treatment of *Staphylococcus epidermidis*-associated septicaemia, peritonitis or endocarditis.

It will be apparent that the polypeptides identified by the method according to the invention will facilitate the production of therapeutic antibodies to a range of diseases resulting from pathogenic infection, for example, septicaemia; tuberculosis; bacteria-associated food poisoning; blood infections; peritonitis; endocarditis; sepsis; meningitis; pneumonia; stomach ulcers; gonorrhoea; strep throat; streptococcal-associated toxic shock; necrotizing fasciitis; impetigo; histoplasmosis; Lyme disease; gastro-enteritis; dysentery; shigellosis.

As has already been stated earlier, microbial organisms cause a wide variety of diseases. Listed below, and not by way of limitation, are a number of micro-organisms and some of the diseases they cause.

| Micro-organism | Disease(s) caused |
|---|---|
| Staphylococcus aureus | Sepsis, food poisoning, septicaemia, |
| Staphylococcus epidermidis | Peritonitis, septicaemia, endocarditis, other hospital-associated diseases |
| Enterococcus faecalis | Endocarditis, cystitis, wound infections |
| Mycobacterium tuberculosis | Tuberculosis |
| Streptococcus group B | Sepsis, meningitis, pneumonia, bladder infections |
| Streptococcus pneumoniae | Pneumonia, meningitis |
| Helicobacter pylori | Stomach ulcers |
| Neisseria gonorrhoea | Gonorrhoea |
| Streptococcus group A | Strep throat, necrotizing fasciitis, impetigo, Strep. Toxic shock syndrome |
| Borrelia burgdoferi | Lyme disease |
| Coccidiodes immitis | Pneumonia |
| Histoplasma sapsulatum | Histoplasmosis, pneumonia |
| Neisseria meningitidis type B | Meningitis |
| Shigella flexneri | Gastro-enteritis, shigellosis, dysentry |
| Escherichia coli | Food-poisoning, gastro-enteritis |
| Haemophilus influenzae | Meningitis, pneumonia, arthritis, cellulitis |

An embodiment of the invention will now be described by example only and with reference to the following materials, methods and SEQ ID NO's 1-19 and Table 1.

Materials and Methods

A λZAP Express library of genomic DNA of *S. aureus* 8325/4 was used. It contains fragments of 2-10 kb from a partial Sau3A digest of total genomic DNA. This was cloned into the BamH1 site of the vector. The library contains >10× coverage of the genome. The library was probed by plaque lift using an initial screen of approximately 20,000 plaque forming units on a 9 cm diameter Petri dish. The plating cells used, their treatment, the plating procedure and buffers were exactly as described in the manufacturers handbook (Stratagene). Plating cells, *Escherichia coli* XL1-Blue MRF', were infected with phage and plated in 3 ml top LB agar containing 10 mM MgSO$_4$ onto LB plates containing 10 mM MgSO$_4$. The plates were then incubated at 42° C. for 4 hr. An 8.5 cm diameter nitrocellulose filter disc (previously soaked in 10 mM IPTG and air-dried) was placed on each plate and its location marked. The plates were then incubated for a further 3.5 hr at 37° C. The filters were removed and washed in TBST buffer before blocking overnight at 4° C. in TBST containing 6% w/v dried skimmed milk and 3% v/v pig serum (Sigma). The serum was used to block any Protein A clones on the filter. The filters are then treated with patient serum (1/5000 dilution) in blocking solution for 90 min at room temperature. Antisera have been obtained from patients convalescing from major *S. aureus* infections. The filters are then washed for 3×10 min in TBST. Secondary antibody used was goat anti-human whole IgG alkaline phosphatase linked (Sigma) at 1/30,000 dilution in blocking solution at room temperature for 30 min. The filters were then washed as above and developed using a standard colorimetric procedure.

Cross-reactive plaques were located on the agar plates and cored into 0.2 ml phage buffer with 0.02 ml chloroform. The titre of each core stock was determined and the phage plated at approximately 200 plaques per plate. A plaque lift and screen was performed as above to give single, pure cross-reactive clones.

The pure clones were then spotted (1 µl) onto plates to give a confluent plaque of 0.5 cm diameter. 30 individual clones can be spotted on each plate. A plaque lift is performed and the filter probed with an appropriate sera. In this way clones can be tested for their cross-reactivity with other patient sera, non-infected donor sera and anti-Protein A sera.

Individual clones were then excised to give a phagemid in *E. coli* XLOLR using the manufacturers protocol (Stratagene). A plasmid miniprep of each was carried out and the size of the genomic insert determined by restriction mapping. The identity of the cloned insert was determined by DNA sequencing using primers against vector sequence, which allows sequencing across the insert. By comparison of the derived sequence against the public domain databases the nature of the cloned gene(s) can be determined.

Hybridisation Solutions/Conditions

Typically, hybridisation conditions uses 4-6×SSPE (20× SSPE contains 175.3 g NaCl, 88.2 g NaH$_2$PO$_4$H$_2$O and 7.4 g EDTA dissolved to 1 liter and the pH adjusted to 7.4); 5-10× Denhardts solution (50× Denhardts solution contains 5 g Ficoll (type 400, Pharmacia), 5 g polyvinylpyrrolidone abd 5 g bovine serum albumen; 100 µg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42°-65° C.

*Staphylococcus aureus* clones identified in human sera screen

TABLE 1

| Patient Sera | Clone | Encoded proteins | Locus number |
|---|---|---|---|
| A | 1 | γ hemolysin B and C subunit | 1 |
| A | 3 | Atl | 2 |
| A | 4 | γ hemolysin B and C subunit | 1 |
| A | 5 | γ hemolysin B and C subunit | 1 |
| A | 7 | Novel putative protease (ORF1 novel antigen like) | 7 |
| A | 8 | Novel nuclease (YisK) | 5 |
| A | 9 | Novel autolysin | 6 |
| A | 10 | γ hemolysin B and C subunit | 1 |
| A | 11 | Atl | 2 |
| A | 14 | γ hemolysin B and C subunit | 1 |
| A | 15 | γ hemolysin B and C subunit | 1 |
| A | S1 | Novel putative protease (ORF1 novel antigen like) | 7 |
| A | S5 | Novel surface protein | 12 |
| A | S17 | γ hemolysin B and C subunit | 1 |
| A | S18 | Novel putative protease (ORF1 novel antigen like) | 7 |
| A | S19 | Novel autolysin | 6 |
| A | S20 | Novel surface protein/toxin | 13 |
| A | S21 | γ hemolysin B and C subunit | 1 |
| A | S25 | γ hemolysin B and C subunit | 1 |
| A | S29 | Fibrinogen binding protein | 3 |
| A | S44 | Novel surface protein | 12 |
| A | S45 | Atl | 2 |
| A | S55 | Atl | 2 |
| A | S64 | Atl | 2 |
| A | S66 | Atl | 2 |
| B | 2 | Novel exotoxin (exotoxin 2 like) | 8 |
| C | 1 | Coagulase | 4 |
| C | 2 | Coagulase | 4 |
| C | 3 | Coagulase | 4 |
| C | 4 | Coagulase | 4 |
| C | 5 | Coagulase | 4 |
| C | 6 | Coagulase | 4 |
| C | 7 | Coagulase | 4 |

TABLE 1-continued

| Patient Sera | Clone | Encoded proteins | Locus number |
|---|---|---|---|
| C | 8 | Coagulase | 4 |
| C | 9 | Coagulase | 4 |
| C | 10 | Coagulase | 4 |
| C | 11 | Coagulase | 4 |
| C | 13 | Coagulase | 4 |
| C | 14 | Coagulase | 4 |
| C | 15 | Coagulase | 4 |
| C | 19 | Coagulase | 4 |
| C | 20 | Coagulase | 4 |
| C | 25 | Coagulase | 4 |
| E | 6 | Novel surface proteins | 9/10 |
| E | 7 | Novel surface proteins | 9/10 |
| E | 11 | γ hemolysin B and C subunit | 1 |
| F | 1 | Novel exotoxin (exotoxin 2 like) | 8 |
| F | 2 | Novel exotoxin (exotoxin 2 like) | 8 |
| F | 3 | Novel exotoxin (exotoxin 2 like) | 8 |
| F | 4 | Novel exotoxin (exotoxin 2 like) | 8 |
| F | 5 | Novel hemolysin (YjfD) | 11 |

What is claimed is:

1. A composition for stimulating an immune response comprising a carrier or adjuvant and at least one isolated polypeptide comprising the amino acid sequence of SEQ ID NO: 14.

2. The composition of claim 1, further comprising an isolated polypeptide comprising the amino acid sequence of SEQ ID NO: 28.

3. The composition of claim 2, wherein said polypeptide comprising the amino acid sequence of SEQ ID NO. 28 is a recombinant polypeptide.

4. The composition of claim 3, wherein said recombinant polypeptide is encoded by an isolated nucleic acid molecule characterized in that said nucleic acid molecule is part of an isolated vector adapted to facilitate recombinant expression of said polypeptide encoded by said nucleic acid molecule.

5. The composition of claim 4, wherein said vector is an expression vector adapted for prokaryotic gene expression.

6. The composition of claim 4, wherein said vector is an expression vector adapted for eukaryotic gene expression.

* * * * *